United States Patent [19]
Mabilat et al.

[11] Patent Number: 5,703,217
[45] Date of Patent: Dec. 30, 1997

[54] NUCLEOTIDE FRAGMENT OF THE 23S RIBOSOMAL RNA OF MYCOBACTERIA, DERIVED PROBES AND PRIMERS, REAGENT AND DETECTION METHOD

[75] Inventors: Claude Mabilat, Villeurbanne; Richard Christen, Nice, both of France

[73] Assignee: Bio Merieux, Marcy L'Etoile, France

[21] Appl. No.: 403,762

[22] PCT Filed: Jul. 22, 1994

[86] PCT No.: PCT/FR94/00929

§ 371 Date: Mar. 23, 1995

§ 102(e) Date: Mar. 23, 1995

[87] PCT Pub. No.: WO95/03412

PCT Pub. Date: Feb. 2, 1995

[30] Foreign Application Priority Data

Jul. 23, 1993 [FR] France ................. 93 09318

[51] Int. Cl.⁶ .......... C07H 21/02; C07H 21/04; C12Q 1/68; C12P 19/34
[52] U.S. Cl. .......... 536/23.1; 435/6; 435/91.2; 536/24.32
[58] Field of Search .......... 435/6, 91.2; 536/23.1, 536/24.32

[56] References Cited

U.S. PATENT DOCUMENTS 5,521,300   5/1996   Shah et al. ................. 536/24.32

FOREIGN PATENT DOCUMENTS

EP 0 395 292   10/1990   European Pat. Off. .
WO 93/04201   3/1993   WIPO .

OTHER PUBLICATIONS

Keller and Manak, In DNA Probes and Applications, Stockton Press, 1994, pp. 565–583. (vol. not applicable).
Erlich et al. In PCR Technology, Freeman and Company, pp. 235–244, 1992. (vol. not applicable).
Gura, Science 270: 575–577, 1995.
Gutierrez et al., The Lancet, 339: 715–721, 1992.
Liesack Febs 281: 114, 1991.
Fleurbaaij et al. Genbank Sequence Listing, 1992.
U. Sjöbring et al., "Polymerase Chain Reaction for Detection of Mycobacterium tuberculosis," *J. of Clinical Microbiology*, vol. 28, No. 10, pp. 2200–2204, Oct. 1990.
A.R. Dunn et al., "A Novel Method to Map Transcripts: Evidence for Homology between an Adenovirus mRNA and Discrete Multiple Regions of the Viral Genome," *Cell*, vol. 12, pp. 23–36, Sep. 1977.
M.W. Gray et al., "On the Evolutionary Descent of Organisms and Organelles: A Global Phylogeny Based on a Highly Conserved Structural Core in small Subunit Ribosomal RNA," *Nucleic Acids Research*, vol. 12, No. 14, 1984.
C.R. Woese et al., "Detailed Analysis of the Higher-Order Structure of 16S–Like Ribosomal Ribonucleic Acids," *Microbiology Reviews*, vol. 47, No. 4, pp. 621–669, Dec. 1983.
P.E. Nielsen et al., "Sequence–Selective Recognition of DNA by Strand Displacement with a Thymine–Substituted Polyamide," *Science*, vol. 254, pp. 1497–1500, Dec. 1991.

*Primary Examiner*—W. Gary Jones
*Assistant Examiner*—Dianne Rees
*Attorney, Agent, or Firm*—Oliffe & Berridge, P.L.C.

[57] ABSTRACT

Bacteria of the genus Mycobacterium can be detected and/or identified by methods using probes including fragments of a variable region of a 23S ribosomal RNA of a species of the genus Mycobacterium or probes including DNA fragments that are obtained by reverse transcription of the RNA or that form the RNA by transcription. Primers for the reverse transcription of a variable region of a 23S ribosomal RNA sequence of mycobacteria include nucleotide sequences of a 23S RNA of a species of the genus Mycobacterium.

28 Claims, 11 Drawing Sheets

FIG. 1

```
-------------------------------------------------------         1
-------------------------------------------------------         2
--------------AGAA------------C---------UC-------------         3
---------------*-AA-------------------U----------------         4
---C--C----XC--                                                 5
-----------------A--------------------U----------------         6
-----------------A--------------------UU---------------         7
---------------*-A----------AA*---------UG-------------         8
                                                                9
-----------------A--------------------UG---------------        10
------------------------NA*N----------UG---------------        11
---------------*-A----------AA---------UG--------------        12
                                                               13
-----------------A----------AA---------UG--------------        14
---------------*-A--------------------UG---------------        15
-----------------A--------------------UG---------------        16
-----------------A-A------AN---A*------UG--------------        17
--A-------CG----AA------U----CC-A-------C-C------C--------     18
CUCAGUACCCGUAGGAGGAGAAA*ACAA*UUGUGA*UUCCGCA/AGUAGUGGCGAGCGA
    |                                       |
   206                                     248
```

FIG. 2

```
-------------------------------------------------------         1
---------------G---------------------------------------         2
--------------*---------------------U-----AC-----------         3
------------NA--N-A-U---------------------UU-----------         4
                                                                5
-------------------------------------U-AU--------------         6
---------A----A--------------------U------A------------         7
---------A----G-GG-U----------UG-A----U-AU---C--C----*----      8
                                                                9
------------U--G--U-U-------------A----UC----UA--------        10
---------A----G-GG-U----------UG-A----U-AU---C--C------        11
---------A--**--GG-U----------*-U-----U-AU------               12
                                                               13
---------A----G-GG-U----------U-U-----U-AU*------------        14
---------A----G-GG-U----------GU------U-AU---C--CG------       15
---------A----G-GG------------UGU-----U-AU---C--CG------       16
---------A----G-GG-U---G------U-U-----U-AU-----X-------        17
--------------G----G----C-C-G-G-CUGAAUCA-U--GUG************    18
GGCGAGCGAACGCG/*AACA*GGCUAAACCGCACGCAUGGGUAACCGGGUAGGGGUUGU
               |                    |
              269                  289
```

```
------------------------------------------------------------    1
----------------------C-G-CAC-UGC-*---------------------        2
----------------------C-G-CAC-UGCU**UA------CA----------        3
------------------U------C-G-CAC-UGC-*--------C------A------    4
                              *--UGUGU-XX--------------         5
--------------------C-GUCAC-UAC-*-U------N-------------         6
-----A----------------C-G-CAC-UAC-*-U-------CA----------        7
--------U--C---G-U------A-A-UGCU---U*AGUG--GUG-C-----------     8
                                                                9
----------A----------G-CUG-CAC-UGC-*-U------------------        10
--------------G-U------A---UGCU---U*AGUG--GUG-C-----------      11
------------------U------C-GACGU-UGU-*-U-AUGGUG-------------    12
                                                                13
-----------------U-----CUGACAU-UAC-AAGAACGGUG-------------      14
----------C---AC-------AUGCUGC*----*-GUC-CAGG-------------      15
--------U--U---G--------AUGCA-U-UGU**-GUGGAAUG--------------    16
-----------------U------C-GACGU-UGU-*-U-AUGGUG-------------     17
-----C-----C----A-A----UG-ACAUG-UGUG******AGC-CGAU------GGC     18
GGUGAGAGCCCGGUACGCGAAAACNCCGGCACCUGCCUAGUAUCAAUUCCCGAGUAGCAG
 |                                                          |
341                                                         372
```

FIG. 5

```
------------------------------------------------------------    1
                                                                2
---------*AU--C-UU*G-G----****-------------------A------        3
---------UAU--CGUAAG-G----****--------------------------        4
                                                                5
---------*AU--C-UU**-G----****--------------------------        6
---------CAU--C-UU***G----****--------------------------        7
---------UAU---C--AACA-----UGGNGU------------------U------      8
                                                                9
-----------A-G-GU-A-------U**---------------------------        10
---------UAU---C--AACA-----UGGUGU------------------U------      11
---------UAU---C--AA-A-----UGGUGU------------------U------      12
                                                                13
---------UAU--GC--AGUA-----UGGUGU------------------U------      14
---------UAU--------UA--UG-UG-UGGUGU---------------U------      15
---------UAU---GUGAG------****--------------------------        16
---------UAU---C--AA-A-----UGGUGU------------------U------      17
CU------UA******************---------------------U--AG-G-A-    18
UAGGGCG*AUCCCAUACGCGCGUGUGAAU**************AGUGGCGUGUUCU
 |                                                      |
645                                                    661
```

---------U-G------------------------------------------------------
---------U-G------------------------------------------------------
---------U-G------------------------------------------------------
---------U-G------------------------------------------------------
-------U-U-GU-A---------------------------------------------------
GGGAGCGUCCC*UCAU**************************************************
           |
          1201
```

FIG. 7A

```
------------------------------------------------------------------     1
-------------------A*-----A---------------------------------------     2
-------------------U----------------------------------------------     3
-------------------UG--------A-----*---------A--------------------     4
---------C-G-U-----AG---A-A----U-UA-CU----------CU--U-------------     5
-------------------U----------------------------------------------     6
---------G---------U---------A---------------UU-------------------     7
---------C-G-U-----AG---A-A----U-UA-CU----------U-----------------     8
------------------------------------------------------------------     9
-------------------U---------A-------------------------A----------    10
---------C-G-U-----AG---A-A----U-UA-CU----------UA--GAGUGA--------    11
---------C-G-U------G-----A----U-GA-------------U-----------------    12
------------------------------------------------------------------    13
---------C-G-U-----AG---A-A----U-UA-CU----------U-----------------    14
---------C-G-U-----AG---A-A----U-UA-CU----------U-----------------    15
---------C---U-----AG----------UGUUG---------U--A---A--           16
---------C-G-U------G-----A----U-GA-------------U-----------------    17
---------GC-U------GUG--UGCU----GG-AUGC*-------UAUCA-A----C-          18
*********UCAGCGAAGCCA**CCGGGUGA*CCGGUGG*UGGAGGGUGGGGGAGUGAG
                                       |
                                      1242
```

FIG. 7B

```
1   ------------------------------------------------------------
2   ------------------------------------------------------------
3   ---------------A--*GCGUCCC*----------G----------------------
4   ---------------CGCG*CCCG---------G-G------------------------
5   ---------------AGCGUCCC*----------G----------G--------------
6   ---------------A---GCGUCCC*----------G----------------------
7   ---------------*GCGUCCC*----------G-------------------------
8   ---------------AGCGUCCC*----------G----------G--------------
9   ------------------------------------------------------------
10  ----------------UGCG*CCCG---------G------C------------------
11  ---------------AGCGUCCC*---------*----------G---------------
12  ---------------A--UGCGUCCA*----------G-----------U----------
13  ------------------------------------------------------------
14  ---------------A--UGCGUCCC*--------CAUU--G-------U----------
15                                                  -----------
16  ---------------X--AGCGUCCC*----------------G------GG
17  ---------------A--UGCGUCCA*----------G-----------U----------
18  ----U----UU-GUGU-AC********--C*--***************************
    UUCCCGUACCCGUGUGUGGAGCCGUGAUGAUGAAUCACCGGUACUAACCACCCAAAACC
                   |
                 1409
```

FIG. 8A

```
------------------------------------------------------------
----------G-----C-***A----------G-C--U-CC*AU-C------------G
----------G-------C-UA-C-------GGC-*U-GAG-UCC---------------
--------AC-GUC-C-***GA------A--G---A--GA--G--*---------C--G
----------G-----C-***A----------GGC*AU-GAG-U-C------------G
----------G-----C-***A----------G-C-*U-GAG-U-C--------------
--------ACGGUC-C--****AU-------G--NA--CC-CG--*------------G
----------G-----C-AUAUCC--------GGCUAU-GAGGU-C------------G
--------ACGGUC-C--***A----------G---A--CA-G------------C--G
U--------ACCGU----ACA-C-**------G------C---GGU--------A---G

U---------UCGU--CU-****AU-------G---A--C---GAC------------G
----------UGGC-----*****AU-------G---AC-GU-***G-------N----G
-------GGUG-G-AGAUCUAGAAU---------AAA---C-GU---CC------C--G
U--------ACCGU--C--CA-C*U*------G------C---GGU--------A---G
********-********************--*********-**************
CCCAAAACCG*AUCGAUCGACCUUCCUUCGGG**UGUGGAGUUCU*GGGGCUGCGUGGA
```

FIG. 8B

```
                                                                      1
                                                                      2
C*AU-C-----------G-C--------------------A---U----------               3
AG-UCC-------------C-----U----------------C---C----------             4
A--G--*--------C-G-C-----U--------------------U----------             5
AG-U-C-----------G-C--------------------A---U----------               6
AG-U-C-------------C--------------------A---U----------               7
C-CG--*-----------G-C-----U-C--U--------------U----------             8
                                                                      9
AGGU-C-----------G-A-----U-------------------U----------             10
A--G----------C--G-C-----U-------------------U----------             11
---GGU--------A---G-C-----U-------------------U----------            12
                                                                     13
---GAC-----------G-C-CCG-UG-------------------U----------            14
U-***G-------N----G-CNNGG-UG-------------------U----------           15
C-GU---CC------C--G-------G-------------------U----------            16
---GGU--------A---G-C-----U-------------------U----------            17
*****-*************-*******************--------G----G--             18
GUUCU*GGGGCUGCGUGGAA*CUUCGCUGGUAGUAGUCAAGCGA**AGGGGUGACGCAG
                                     |
                                   1420
```

FIG. 8C

```
1     -- GUGUGGAGCCGUGAUGAUGAAUCACCGGUACUAACCACCCAAAACC
19    ---      G--GACCG---C------G---------------------
29    ---      G--GACCG---C------G---------------------
20    --- GUAU-G--GUCCC----------G--C------------------
21    CCGUGUAUAG--GUCCC----------G---------------------
6     CCGUGUAU-G--GUCCC----------G---------------------
22    CCGUGUAU-G--GUCCC----------G---------------------
23    CCGUGUAU-G--GUCCC----------G---------------------
24    CCGUGUAUAG--GUCCC----------GU-----------------UGG
12    CCGUGUAU-U--GUCC-----------G-----------U--------
16    CCGUGNU----GUCCC-----------------------G------GG
14    CCGUGUAU-U--GUCCC---------CAUU--G-------U--------
25                 CCG--------G---------------------
15    CCGUGUAU----GUCCC---------CAUUC-G----------------
26    --- N-CCN--GNCCC---C--N-CAUUC-G-------------UGG
17    CCGUGUAU-U--GUCC-----------G-----------U--------
8     CCGUGUGU----GUCCC---------G-----------G--------
27       ---CCG--GACCG----------G---------------------
28    ---    CCA*-ACC-----GGAUC-G-------------CGG
E.coli UUG----UAC*******--C*--**********************
         GUGUGGAGCCGUGAUGAUGAAUCACCGGUACUAACCACCCAAAACC
         |
       1409
```

FIG. 9A

```
GAUCGAUCG*ACCUUCCUUCGGGUGUGGAGUUCU***GGGGCUGCGUGGA----------------
-GAUCGAUC---UCC--------G---UG-AGU-CU------------G *         ---------
-GAUCGAUC---UCC--------G---UG-AGU-CU------------G*A*ACUU
-GAUCGA-C--UUCC--------G-C-UG-CGA-UC------------G*A*CCUUCGCUGGUAGU
-GAUCGA-C--UUCC--------G-CAUG-AGU-UC------------G*A*CCUUCGCUGGUAGU
-GAUCGA-C--UU**--------G-CAUG-AGU-UC------------G*A*CCUUCGCUGGUAGU
-GAUCGA-C--UUCC--------G-CAUG-AGU-UC------------G*A*CCUUCGCUGGUAGU
-GAUCGA-C--UUCC--------G-CAUG-CGA-UC------------G*A*CCUUCGCUGGUAGU
UGGUCUAUC--AUNC-----*N-G----*C-AGGAUCACC---------G*A*CCUUCGCUGGUAGU
ACCGUGAUC-*A-AC-U------G*---UG-CGU-GGU--------A---G*A*CCUUCGUUGGUAGU
UGAGC-GAUCUAGAAU-------**AAAG-ACUGUU--CC------C---G*A*C*UUCGGUGGUAGU
-UCGUGA-UG****AU-------G*---AG-CGU-GAC------------G*A*CCCCGGUGGGUAGU
-GAUCGAUC---UCC--------G-C-UG-CGG-CU---C----------**A*GCCUU
UGG-CGAUC-***A---------G*---AC-*GU---G------------G*A*CNNNNNNNNNNAGU
CGGUCUAUC-*AA-C--------G*---CGAAG-AUCGCC----------G*A*CCCGGGUGGGUAGU
ACCGUGA-CG**-AC-U------G*---UG-CGU-GGU--------A---G*A*CCUUCGUUGGUAGU
ACGGUCA-CG***A-*-------G*-NAG-CCUCGU-*------------G*A*CCUUCGUUCGUUGU
-GAUCGAUC---UCC--------G-C-UG-AGG-CU--------------**A*GCCUCCGCUGG
UGGGUGAUCAC*GCC-U------G---UG-GG-CCG-CCC--------GG**CCCGGUCCGCUAGU
*******-*****************---*********************
GAUCGAUCG*ACCUUCCUUCGGGUGUGGAGUUCU***GGGGCUGCGUGGA
```

FIG. 9B

```
---------------------------------     1
     *     -------------------------  19
*A*ACUU                         ----  29
*A*CCUUCGCUGGUAGUAGUCAAGCAAUGGGG--    20
*A*CCUUCGCUGGUAGUAGUCAAGCGA*****U     21
*A*CCUUCGCUGGUAGUAGUCAAGCAA*****U      6
*A*CCUUCGCUGGUAGUAGUCAAGCGA*****U     22
*A*CCUUCGCUGGUAGUAGUCAAGCAA*****U     23
*A*CCUUCGCUGGUAGUAGUCAAGCGA*****U     24
*A*CCUUCGUUGGUAGUAGUCAAGCGA*****U     12
*A*C*UUCGGUGGUAGUAGUCAAGCGA*****U     16
*A*CCCCGGUGGGUAGUAGUCAAGCGA*****U     14
*A*GCCUU                    --------- 25
*A*CNNNNNNNNNNAGUAGUCAAGCGA*****U     15
*A*CCCGGGUGGGUAGUAGUCAAGCAA*****U     26
*A*CCUUCGUUGGUAGUAGUCAAGCGA*****U     17
*A*CCUUCGUUCGUUGUAGUCAAGCGA*****U      8
*A*GCCUCCGCUGG              --------- 27
GCCCGGUCCGCUAGUAGGUAAGCGA***G     28
****************************A        E.coli
                                       |
                                      1420
```

FIG. 9C

```
------------------------------------------------------------------       1
---------U---------G--A-U******--CU--U-C------CGC---------               2
--------------------CGCUCA--***--------------UGC---------                3
--------------------CGU-A-U****--------------UGC---------                4
---CAU-C----X-------GAU-UCA-A***U------------UGC---------                5
--------------------CGCUCAU***---------------UGC---------                6
--------------------CGCUCA-C***--------------UGC---------                7
---CAU-C------C-----GAU-GNN-A***C------------UGC---------                8
                                                                         9
--------------------CGUUCGUG***--------------UGC---------               10
---CAU-C------------GAU-UCA-A***U------------UGC---------               11
--UCA-------U-------CU-GCGUA***U-------------UGC---------               12
                                                                        13
---AAC-G------------C-UUUCA-A***U------------UGC---------               14
C---U---------------CAA-AAUG***-UG-----------UGC---------               15
C---U---------------CACUCAUA***UGU-----------UGC---------               16
--UCA-------U-------CU-GCAUA***U-------------UGC---------               17
U-GUUUUCC-----------GAAAAUC*****--GG-----GC----UGACG-------             18
AGAGCG*AUAGGCAAAUCCGUGCGCGUCUACUAAUCCUGAGAGGUGAGCGAUAG*
       |                                       |
      1493                                    1545
```

```
------------------------------------------------------------  1
-----------------------------------------U------N---------   2
----------------------------------U--                         3
---------------------------------U--U-----------              4
-----------------G----G----**UUC--G----------X------------    5
------------------------------*-U---*---------------------    6
------------------------------*-U---*---------------------    7
-----------------G----------**UUC--G----------U-----------    8
----------------------------C--GC*------------U-----------    9
---------------------U---------A--------------------------  10
-----------------G--------*-*-**UUC--G--------U-----------  11
------------------------GU---UUU*--GG--------------N------  12
-------------------------C--GC*---------------------------  13
---------------------U---------**UUC--G-----------A-------  14
-------------------------C--UUUGC--GG---------------------  15
---------------------U---------*UUUC--GG------------------  16
-------------------------CU---UUU*--GG--------------------  17
----------UU-AUGGG----GCG-AA******-----C-----UCUUG--CG----  18
GGAAGGUUAAGAGGACCCGUUAACCCGCAAGG**GUGAAGCGGAGAAUUUAAGCC
          |                              |
         1854                           1876
```

FIG. 12

```
------------------------------------------------------------  1
------------------------------------------------------------  2
-------------U----G-ACA----------U-U-----U----------------   3
--------------------UC-A---------------------A------------   4
------------------------------------------------------------  5
--------------------UACA---------U-U----AU----------------   6
---------------------C-A----------------------------------   7
-------------------G-GG-C--------G-UU----U----------------   8
-U---------C-UCUA---------*-------U-----------------------   9
-------------------U-------U------------U-----------------  10
-------------------G-GG-C--------G-UU----U----------------  11
-------------------G-UCAC--------GU------U----------------  12
------------------------------------------------------------ 13
-------------------G-AG-C----------UU----U----------------  14
-------------------G-U-------------C-----U----------------  15
-------------------G-AGUA---------AUU----U----------------  16
-------------------G-UCAC--------GU------U----------------  17
----------G--U----GUG-G---------CU-C----AU----C--AC-C-----  18
UAGGUGGGAGACUGUGAAACCUCGACGCCAGUUGGG****GCGGAGUCGUU*GUUGAAA
          |                                     |
         2126                                  2161
```

FIG. 13

NUCLEOTIDE FRAGMENT OF THE 23S RIBOSOMAL RNA OF MYCOBACTERIA, DERIVED PROBES AND PRIMERS, REAGENT AND DETECTION METHOD

BACKGROUND

The present invention belongs to the field of techniques of detection and/or identification of bacteria of the genus Mycobacterium, and more especially of those which use a genetic marker.

The importance of a reliable and sufficiently rapid bacterial diagnosis has been highlighted again with the current epidemic of acquired immunodeficiency syndrome (AIDS), which is giving rise, on the one hand to a resurgence of cases of tuberculosis due to *Mycobacterium tuberculosis, Mycobacterium bovis, Mycobacterium africanum* and *Mycobacterium microti*, species taxonomically very closely related and grouped together under the name "*M. tuberculosis* complex", and on the other hand to the appearance of atypical mycobacterial infections caused, more especially, by *Mycobacterium intracellulare, Mycobacterium avium* and *Mycobacterium paratuberculosis*, gathered under the name "avian complex".

Thus, the technique using a genetic marker in a method of detection by hybridization of nucleic acids, combining specificity, sensitivity and speed, has already formed the subject of several specific applications to the diagnosis of mycobacteria.

More especially, the ribosomal RNA of the bacteria is used as target since, in the first place, it is to be found in substantial amounts in all cells of all living organisms, and secondly it possesses a particular nucleotide sequence made up of a succession of regions characterized by a variable rate of evolution.

The taxonomic value of the 16S and 23S ribosomal subunits of various bacterial species has been demonstrated in hybridization processes for quantifying levels of homologies between these species. Thus, Woese et al., Microbiological Reviews 47:621–669 (1983), and Grayet et al., Nucleic Acids Research 12:5837–5852 (1984) show, by comparisons of 16S RNA sequences, that highly conserved regions are interspersed with regions of moderate and low homologies, even in the case of closely related species.

Patent Application WO-88/03957 describes detection probes specific for mycobacteria, the nucleotide sequences of which are capable of hybridizing with the 16S and 23S subunits of the ribosomal RNAs of said bacteria.

The probes described are 7 species probes, or probes for groups of species, and 4 genus probes, and are gathered in Table 1 below in which are listed, respectively, the target ribosomal RNA subunit, the target nucleotide sequence, taking as reference the nucleotide sequence of *E. coli* ribosomal RNA, and the specificity of the probes with respect to the species, the group of species or the genus Mycobacterium.

TABLE 1

| PROBE No. | Ribosomal RNA subunit | Position in the sequence | Species |
|---|---|---|---|
| 1 | 16S | 185–225 | *M. avium* |
| 2 | 16S | 185–225 | *M. intracellulare* |
| 3 | 16S | 185–225 | *M. tuberculosis* complex |
| 4 | 23S | 1155–1190 | *M. tuberculosis* complex |
| 5 | 23S | 540–575 | *M. tuberculosis* complex |

TABLE 1-continued

| PROBE No. | Ribosomal RNA subunit | Position in the sequence | Species |
|---|---|---|---|
| 6 | 23S | 2195–2235 | *M. tuberculosis* complex |
| 7 | 23S | 2195–2235 | *M. tuberculosis* complex |
| 8 | 16S | 1025–1060 | genus *Mycobacterium* |
| 9 | 23S | 1440–1475 | genus *Mycobacterium* |
| 10 | 23S | 1515–1555 | genus *Mycobacterium* |
| 11 | 23S | 1570–1610 | genus *Mycobacterium* |

It is apparent from this table that, at the species level, only two probes have been developed, one specific for the species *M. avium*, the other specific for the species *M. intracellulare*, and they have been developed on the basis of the sequencing of the 16S ribosomal subunits.

While two species of the "avian complex" which are very closely related from the taxonomic standpoint can be independently identified by these methods, the same does not yet apply to the different species of the "tuberculosis complex".

It emerges, in addition, from this prior art that, on the one hand the regions which are variable from one species to another or from one species to a group of species and which have been adopted for producing probes are located on the 16S subunit of the ribosomal RNA, and that on the other hand the 23S subunit comprises regions which are homologous within the genus Mycobacterium, enabling groups of species of mycobacteria to be detected.

According to the teaching of WO93/04201, some authors have sought, on the basis of the partial determination of the nucleotide sequences of the 23S subunit of the ribosomal RNA of a few pathogenic mycobacteria, to develop species probes which, by specific hybridization, would enable a species of mycobacteria to be detected selectively. The experimental results demonstrated, however, that the probes produced were genus probes specific for mycobacteria or group probes for the tuberculosis or avian group, but that they did not in any case permit the selective detection of species of mycobacteria.

At the present time, no detection technique is simultaneously specific, sensitive and fast enough to diagnose the presence of a particular species of mycobacteria in a biological sample.

BRIEF DESCRIPTION OF THE DRAWINGS

FIGS. 1–13 compare nucleotide sequences of 23S ribosomal RNA of various species of the genus Mycobacterium to corresponding nucleotide sequences of *E. coli*. For each mycobacterial sequence, the nucleotide numbers correspond to their position relative to the nucleotide sequence of *E. coli* 23S ribosomal RNA.

In each Figure, the bottom sequence represents the nucleotide sequence of *M. tuberculosis*. In the other sequences, each hyphen ("-") indicates that the nucleotide at this position corresponds to the nucleotide in *M. tuberculosis* below. Asterisks represent the absence of a nucleotide. They are inserted in order to demonstrate how the various sequences line up. In addition, "N" and "X" represent A, G, C, U or an unknown base. Further, "/" represents A, G, C, U, an unknown base or the absence of a base.

In particular, FIG. 1 demonstrates the sequence of nucleotide Nos. 137 to 179 of species of genus Mycobacterium, as compared to the corresponding sequence of *E. coli*.

FIG. 2 demonstrates the sequence of nucleotide Nos. 206 to 248 of species of genus Mycobacterium, as compared to the corresponding sequence of *E. coli*.

FIG. 3 demonstrates the sequence of nucleotide Nos. 269 to 289 of species of genus Mycobacterium, as compared to the corresponding sequence of E. coli.

FIG. 4 demonstrates the sequence of nucleotide Nos. 289 to 290 of species of genus Mycobacterium, as compared to the corresponding sequence of E. coli.

FIG. 5 demonstrates the sequence of nucleotide Nos. 341 to 372 of species of genus Mycobacterium, as compared to the corresponding sequence of E. coli.

FIG. 6 demonstrates the sequence of nucleotide Nos. 645 to 661 of species of genus Mycobacterium, as compared to the corresponding sequence of E. coli.

FIGS. 7A-7B demonstrate the sequence of nucleotide Nos. 1201 to 1242 of species of genus Mycobacterium, as compared to the corresponding sequence of E. coli.

FIGS. 8A-8C demonstrate the sequence of nucleotide Nos. 1409 to 1420 of species of genus Mycobacterium, as compared to the corresponding sequence of E. coli.

FIGS. 9A-9C demonstrate the sequence of nucleotide Nos. 1409 to 1420 of species of the genus Mycobacterium, as compared to the corresponding sequence of E. coli.

FIG. 10 demonstrates the sequence of nucleotide Nos. 1493 to 1515 of species of the genus Mycobacterium, as compared to the corresponding sequence of E. coli.

FIG. 11 demonstrates the sequence of nucleotide Nos. 1703 to 1761 of species of the genus Mycobacterium, as compared to the corresponding sequence of E. coli.

FIG. 12 demonstrates the sequence of nucleotide Nos. 1854 to 1876 of species of the genus Mycobacterium, as compared to the corresponding sequence of E. coli.

FIG. 13 demonstrates the sequence of nucleotide Nos. 2126 to 2161 of species of the genus Mycobacterium, as compared to the corresponding sequence of E. coli.

DETAILED DESCRIPTION OF THE INVENTION

According to the present invention, regions which are variable within the genus Mycobacterium have been determined on the ribosomal RNA of the 23S subunit, thereby making it possible to meet the current need to diagnose a pathogenic agent, in particular in immunosuppressed subjects, by providing detection probes specific for the species and groups of species of mycobacteria.

The starting point of the invention is the complete determination of the nucleotide sequences of the 23S subunit of the ribosomal RNA for a sufficient number of species of mycobacteria, which made it possible to demonstrate several variable regions enabling several species of mycobacteria to be discriminated.

Before describing the invention, various terms used in the description and the claims will now be defined:

- according to the invention, a nucleotide fragment or an oligonucleotide is an arrangement of monomers, characterized by the informational sequence of the natural nucleic acids, which are capable of hybridizing with a nucleotide fragment under predetermined conditions, it being possible for the arrangement to contain monomers of different structures and to be obtained from a molecule of natural nucleic acid and/or by genetic recombination and/or by chemical synthesis,

- thus, a monomer can be a natural nucleotide of nucleic acid whose constituent elements are a sugar, a phosphate group and a nitrogenous base; in RNA the sugar is ribose, in DNA the sugar is 2-deoxyribose; depending on whether the nucleic acid is DNA or RNA, the nitrogenous base is chosen from adenine, guanine, uracil, cytosine and thymine; or a nucleotide modified in at least one of the three constituent elements; as an example, the modification can occur in the bases, generating modified bases such as inosine, 5-methyldeoxycytidine, deoxyuridine, 5-(dimethylamino)deoxyuridine, 2,6-diaminopurine, 5-bromodeoxyuridine and any other modified base promoting hybridization, in the sugar, namely the replacement of at least one deoxyribose by a polyamide [P. E. Nielsen et al., Science, 254, 1497–1500 (1991)], and in the phosphate group, for example its replacement by esters chosen, in particular, from diphosphate, alkyl- and arylphosphonate and phosphorothioate esters,

- "informational sequence" is understood to mean any ordered succession of monomers whose chemical nature and order in a reference direction constitute an item of information of the same quality as that of the natural nucleic acids,

- "hybridization" is understood to mean the process during which, under suitable conditions, two nucleotide fragments having sufficiently complementary sequences pair to form a double strand,

- a probe is a nucleotide fragment comprising from 5 to 100 monomers, and advantageously from 8 to 50 monomers, possessing a specificity of hybridization under particular conditions to form a hybridization complex with a nucleotide fragment having a nucleotide sequence included in the ribosomal RNA, the DNA obtained by reverse transcription of said ribosomal RNA and the DNA of which said ribosomal RNA is the transcription product; a probe may be used for diagnostic purposes, such as capture and/or detection probes, or for therapeutic purposes,

- the capture probe may be immobilized on a solid support by any suitable means, that is to say directly or indirectly, for example by covalent bonding or passive adsorption,

- the detection probe is labeled by means of a label chosen from radioactive isotopes, enzymes chosen, in particular, from peroxidase and alkaline phosphatase and those capable of hydrolyzing a chromogenic, fluorogenic or luminescent substrate, chromophoric chemical compounds, chromogenic, fluorogenic or luminescent compounds, nucleotide base analogs and biotin,

- the probes used for diagnostic purposes of the invention may be employed in all known hybridization techniques, and in particular the techniques termed "dot-blot" [MANIATIS et al., Molecular Cloning, Cold Spring Harbor, (1982)], "Southern blot" [SOUTHERN, E. M., J. Mol. Biol., 98, 503 (1975)], "northern blot", which is a technique identical to the "Southern blot" technique but which uses RNA as target, and the sandwich technique [DUNN A. R., HASSEL J. A., Cell, 12, 23 (1977)]; advantageously, the sandwich technique is used in the present invention, comprising a specific capture probe and/or a specific detection probe, on the understanding that the capture probe and the detection probe must possess an at least partially different nucleotide sequence,

- another application of the invention is a therapeutic probe for treating infections due to mycobacteria, said probe being capable of hybridizing in vivo with the 23S ribosomal RNA of said bacteria and/or with the genomic DNA to block the phenomena of translation and/or transcription, a primer is a probe comprising from 5 to 30 monomers, possessing a specificity of hybridization under particular conditions for the initiation of an enzymatic polymerization, for example in an amplification technique such as PCR (polymerase chain reaction), in an elongation method, such as sequencing, in a method of reverse transcription or the like, homology characterizes the degree of similarity of two nucleotide fragments compared.

In particular, the probes and primers are those whose sequences are identified below, or those which display at least 70% homology and possess at least 5 consecutive monomers of informational sequence identical with these sequences.

According to the invention, and under conditions which will be described in detail later in the text, the nucleotide sequence of the 23S ribosomal RNAs was determined for 16 species of mycobacteria, on the basis of which sequencing single-stranded nucleotide fragments belonging to variable regions, and which are hence specific to one species of mycobacteria, were defined.

To define these fragments and to align them, the numbering of the nucleotide sequence of *Escherichia coli* 23S ribosomal RNA, completely identified by Brosius et al. (1980; Proc. Natl. Acad. Sci. USA; 77: 201–204), was used as reference.

The single-stranded nucleotide fragments of the invention possess a nucleotide sequence chosen from the following sequences:

beginning at nucleotide No. 137 and ending at nucleotide No. 179, beginning at nucleotide No. 206 and ending at nucleotide No. 248, beginning at nucleotide No. 269 and ending at nucleotide No. 289, excluding the fragments of the 23S ribosomal RNA of *M. tuberculosis* and of *M. fortuitum*, beginning at nucleotide No. 289 and ending at nucleotide No. 290, excluding the fragments of the 23S ribosomal RNA of *M. tuberculosis* and of *M. fortuitum*, beginning at nucleotide No. 341 and ending at nucleotide No. 372, beginning at nucleotide No. 645 and ending at nucleotide No. 661, excluding the fragments of the 23S ribosomal RNA of *M. tuberculosis* and of *M. fortuitum*, beginning at nucleotide No. 1201 and ending at nucleotide No. 1242, beginning at nucleotide No. 1409 and ending at nucleotide No. 1420, excluding the fragments of the 23S ribosomal RNA of *M. tuberculosis*, of *M. marinum*, of *M. scrofulaceum*, of *M. avium* TMC 724, of *M. leprae*, of *M. kansasii* and of *M. asiaticum*, of *M. ulcerans* ATCC 19423, *M. malmoense* ATCC 29571, *M. gordonae*, *M. lactae* ATCC 25854, *M. aurum* ATCC 23366, *M. vaccae* ATCC 15483 and *M. neoaurum* ATCC 25795, beginning at nucleotide No. 1493 and ending at nucleotide No. 1515, beginning at nucleotide No. 1703 and ending at nucleotide No. 1761, beginning at nucleotide No. 1854 and ending at nucleotide No. 1876, excluding the fragments of the 23S ribosomal RNA of *M. tuberculosis*, of *M. kansasii* and of *M. fortuitum*, beginning at nucleotide No. 2126 and ending at nucleotide No. 2161, excluding the fragments of the 23S ribosomal RNA of *M. tuberculosis*, of *M. kansasii* and of *M. fortuitum*, and their complementary sequences, the numbers of the nucleotides corresponding to their position relative to the nucleotide sequence of *Escherichia coli* 23S ribosomal RNA, used as reference.

More especially, the nucleotide sequences of the fragments of the invention are chosen from the sequences SEQ ID NO 1 to SEQ ID NO 28, SEQ ID NO 30 to SEQ ID NO 37, SEQ ID NO 39 to SEQ ID NO 41, SEQ ID NO 43 to SEQ ID NO 49, SEQ ID NO 51 to SEQ ID NO 67, SEQ ID NO 69 to SEQ ID NO 75, SEQ ID NO 77 to SEQ ID NO 93, SEQ ID NO 95, SEQ ID NO 97, SEQ ID NO 98, SEQ ID NO 100 to SEQ ID NO 136, SEQ ID NO 138 to SEQ ID NO 144, SEQ ID NO 146 to SEQ ID NO 148, SEQ ID NO 150 to SEQ ID NO 152, SEQ ID NO 154 to SEQ ID NO 158, SEQ ID NO 160, SEQ ID NO 161, SEQ ID NO 163 to SEQ ID NO 174 and SEQ ID NO 178, and their complementary sequences.

The numbering of the *E. coli* 23S rRNA sequence applied to the sequences identified in the present description does not always reflect the number of nucleotides or monomers constituting these sequences. In effect, mycobacteria possess additional genetic material relative to *E. coli*, which is especially conspicuous for the sequences SEQ ID NO 94 to 106 and SEQ ID NO 29 to SEQ ID NO 41.

According to the above definition, the fragments of the invention are RNA fragments, but they can also be single-stranded fragments of DNA resulting from the reverse transcription of the abovementioned RNA fragments, or their complementary fragments, as well as single-stranded fragments of genomic DNA whose transcription products are the abovementioned RNA fragments, or their complementary fragments.

Preferred probes are those possessing a sequence chosen from the sequences:

beginning at nucleotide No. 10 and ending at nucleotide No. 24 of the variable region corresponding to the sequences SEQ ID NO 1 to 14, beginning at nucleotide No. 26 and ending at nucleotide No. 45 of the variable region corresponding to the sequences SEQ ID NO 1 to 14, beginning at nucleotide No. 1 and ending at nucleotide No. 20 of the variable region corresponding to the sequences SEQ ID NO 15 to 28, beginning at nucleotide No. 26 and ending at nucleotide No. 43 of the variable region corresponding to the sequences SEQ ID NO 15 to 28, beginning at nucleotide No. 4 and ending at nucleotide No. 22 of the variable region corresponding to the sequences SEQ ID NO 29 to 41, beginning at nucleotide No. 12 and ending at nucleotide No. 29 of the variable region corresponding to the sequences SEQ ID NO 42 to 53, beginning at nucleotide No. 36 and ending at nucleotide No. 56 of the variable region corresponding to the sequences SEQ ID NO 42 to 53, beginning at nucleotide No. 13 and ending at nucleotide No. 32 of the variable region corresponding to the sequences SEQ ID NO 54 to 67, beginning at nucleotide No. 5 and ending at nucleotide No. 23 of the variable region corresponding to the sequences SEQ ID NO 68 to 79, beginning at nucleotide No. 15 and ending at nucleotide No. 33 of the variable region corresponding to the sequences SEQ ID NO 80 to 93, beginning at nucleotide No. 1 and ending at nucleotide No. 21 of the variable region corresponding to the sequences SEQ ID NO 94 to 106 and SEQ ID NO 166 to 178, beginning at nucleotide No. 44 and ending at nucleotide No. 76 of the variable region corresponding to the sequences SEQ ID NO 94 to 106 and SEQ ID NO 166 to 178, beginning at nucleotide No. 67 and ending at nucleotide No. 85 of the variable region corresponding to the sequences SEQ ID NO 94 to 106 and SEQ ID NO 166 to 178, beginning at nucleotide No. 6 and ending at nucleotide No. 26 of the variable region corresponding to the sequences SEQ ID NO 107 to 120, beginning at nucleotide No. 1 and ending at nucleotide No. 18 of the variable region corresponding to the sequences SEQ ID NO 121 to 136, beginning at nucleotide No. 39 and ending at nucleotide No. 55 of the variable region corresponding to the sequences SEQ ID NO 121 to 136, beginning at nucleotide No. 11 and ending at nucleotide No. 26 of the variable region corresponding to the sequences SEQ ID NO 137 to 152, beginning at nucleotide No. 5 and ending at nucleotide No. 22 of the variable region corresponding to the sequences SEQ ID NO 153 to 165, and their complementary sequences, on the understanding that the numbering of the monomers constituting each probe is reckoned from the beginning of the sequence from which the probe is derived.

An especially advantageous probe of the invention is the one whose nucleotide sequence begins at nucleotide No. 1 and ends at nucleotide No. 21 of the variable region corresponding to SEQ ID NO 94, the importance of which lies in its specificity with respect to the species *M. tuberculosis*, among other species of mycobacteria, but also within the *M. tuberculosis* group itself.

Other particular probes described and tested in the examples which follow are those specific for the species *M. fortuitum* and *M. xenopi*, respectively.

Another subject of the invention is a primer for the specific reverse transcription of a 23S ribosomal RNA sequence of mycobacteria, belonging to a variable region, into a complementary DNA sequence, or a primer, in particular, for the specific amplification, by a polymerase chain reaction, of the DNA sequence complementary to a 23S ribosomal RNA sequence of mycobacteria belonging to a variable region.

The therapeutic probes of the present invention comprise a nucleotide sequence belonging to the sequence of a fragment possessing at least one of the following nucleotide sequences of the 23S RNA:

beginning at nucleotide No. 137 and ending at nucleotide No. 179, beginning at nucleotide No. 206 and ending at nucleotide No. 248, beginning at nucleotide No. 269 and ending at nucleotide No. 289, beginning at nucleotide No. 289 and ending at nucleotide No. 290, beginning at nucleotide No. 341 and ending at nucleotide No. 372, beginning at nucleotide No. 645 and ending at nucleotide No. 661, beginning at nucleotide No. 1201 and ending at nucleotide No. 1242, beginning at nucleotide No. 1409 and ending at nucleotide No. 1420, beginning at nucleotide No. 1493 and ending at nucleotide No. 1515, beginning at nucleotide No. 1703 and ending at nucleotide No. 1761, beginning at nucleotide No. 1854 and ending at nucleotide No. 1876, beginning at nucleotide No. 2126 and ending at nucleotide No. 2161, and their complementary sequences.

The invention also relates to a reagent for detecting and/or identifying at least one species of mycobacteria in a biological sample comprising at least one probe of the invention, and especially a capture probe and a detection probe, one and/or other corresponding to the definition of a probe according to the invention. The reagent can comprise a mixture of probes of the invention with the object of detecting at least two species of mycobacteria.

Lastly, the invention provides a method for selectively detecting and/or for identifying a species of mycobacteria in a biological sample, according to which the 23S ribosomal RNA extracted from the mycobacteria and, where appropriate, denatured, or the genomic DNA extracted from the bacteria and denatured, or the DNA obtained from the reverse transcription of the 23S ribosomal RNA, is exposed to at least one probe of the invention, and the hybridization of said probe is detected.

Preferably, before the DNA is exposed to the probe of the invention, an amplification of this DNA is carried out in the presence of an appropriate enzyme system and at least one amplification primer of the invention.

The origins of the invention and some of its applications are described below in Examples 1 to 5 which follow, reference being made to FIGS. 1 to 13 showing the alignments of the sequences belonging to the variable regions of the 23S RNA for different strains of 20 species of mycobacteria. Among these figures, FIGS. 7, 8 and 9 consist of the alignment of the following Figures, respectively: 7*a* and 7*b*; 8*a*, 8*b* and 8*c*; 9*a*, 9*b* and 9*c*.

More especially, FIGS. 1, 2, 3, 4, 5, 6, 7, 8, 9, 10, 11, 12 and 13 relate to the variable regions in the order of their appearance on the 23S rRNA of mycobacteria, and correspond to the following sequences, respectively:

| | |
|---|---|
| SEQ ID NO | 1 to 14 |
| SEQ ID NO | 15 to 28 |
| SEQ ID NO | 29 to 41 |
| SEQ ID NO | 42 to 53 |
| SEQ ID NO | 54 to 67 |
| SEQ ID NO | 68 to 79 |
| SEQ ID NO | 80 to 93 |
| SEQ ID NO | 94 to 106 |
| SEQ ID NO | 166 to 178 |
| SEQ ID NO | 107 to 120 |
| SEQ ID NO | 121 to 136 |
| SEQ ID NO | 137 to 152 |
| SEQ ID NO | 153 to 165 |

The numbers appearing at the ends of the sequences on the figures each refer to a species of mycobacteria conforming to the correspondences shown in Table 2 below:

9

TABLE 2

| NUMBER | SPECIES |
|---|---|
| 1 | M. tuberculosis |
| 2 | M. BCG |
| 3 | M. africanum |
| 4 | M. marinum |
| 5 | M. vaccae |
| 6 | M. intracellulare |
| 7 | M. scrofulaceum |
| 8 | M. szulgai |
| 9 | M. kansasii |
| 10 | M. leprae |
| 11 | M. terrae |
| 12 | M. chelonae |
| 13 | M. flavescens |
| 14 | M. fortuitum |
| 15 | M. phlei |
| 16 | M. chitae |
| 17 | M. smegmatis |
| 18 | E. coli |
| 19 | M. bovis |
| 20 | M. avium |
| 21 | M. avium θ |
| 22 | M. intracellulare |
| 23 | M. intracellulare |
| 24 | M. intracellulare |
| 25 | M. gastri |
| 26 | M. simiae |
| 27 | M. terrae |
| 28 | M. xenopi |
| 29 | M. bovis BCG |

EXAMPLE 1

Determination of the nucleotide sequence of the 23S ribosomal RNAs of mycobacteria The nucleotide sequence of the 23S ribosomal RNA of the following 16 strains was determined:

| M. tuberculosis | A 203 | bioMérieux |
|---|---|---|
| M. bovis BCG | | Pasteur-Nice hospital |
| M. africanum | CIP 140 030 001 | |
| M. intracellulare | CIP 140 310 001 | |
| M. chelonae | A 232 | bioMérieux |
| M. chitae | ATCC 19627 | |
| M. flavescens | CIP 140 230 001 | |
| M. fortuitum | CIP 140 410 001 | |
| M. kansasii | CIP 140 110 001 | |
| M. marinum | CIP 140 120 001 | |
| M. phlei | A 247 | bioMérieux |
| M. scrofulaceum | CIP 140 220 001 | |
| M. smegmatis | A 251 | bioMérieux |
| M. szulgai | A 253 | bioMérieux |
| M. terrae | A 255 | bioMérieux |
| M. vaccae | | bioMérieux |

The total DNA of these strains was isolated by the method of Sjöbring et al. [1990. Polymerase chain reaction for detection of *Mycobacterium tuberculosis*. J. Clin. Microbiol. 28(10):2200–2204]. PCR amplification products which cover 90% of the sequence were generated from the ribosomal DNA using amplification primers of eubacterial specificity.

The amplification products obtained were cloned into the double-stranded forms of phage M13. The recombinant M13 phages obtained served as matrix for the sequencing reaction using the chain termination method (Sanger et al., Proc. Natl. Acad. Sci. USA, 1977, 74: 5463–5467).

EXAMPLE 2

Determination of the nucleotide sequence of the region beginning at nucleotide No. 1409 and ending at nucleotide No. 1420 of the 23S ribosomal RNAs of the following strains of mycobacteria:

| SPECIES | STRAIN | ORIGIN | NUMBER No. (*) |
|---|---|---|---|
| M. bovis | ATCC 19210 | | 19 |
| M. bovis BCG | C 080 | bioMérieux | 29 |
| M. avium | DSM 43216 | | 21 |
| M. intracellulare | ATCC 35764 | | 22 |
| M. intracellulare | ATCC 35767 | | 23 |
| M. intracellulare | ATCC 35847 | | 24 |
| M. gastri | C 097 | bioMérieux | 25 |
| M. terrae | C 104 | bioMérieux | 27 |
| M. simiae | ATCC 25275 | | 26 |
| M. xenopi | C 112 | bioMérieux | 28 |

(*) The numbers refer to FIG. 9.

EXAMPLE 3

Use of a specific probe directed against the 23S ribosomal RNA for the identification of *M. tuberculosis*.

The probe beginning at nucleotide No. 67 and ending at nucleotide No. 85 of SEQ ID NO 94, or its complementary sequence, which is in principle specific for the strains of the *M. tuberculosis* complex, was deduced from the alignments of the nucleotide sequences of 23S ribosomal RNA in FIGS. 8 and 9. It is present in the insertion of genetic material distinctive to mycobacteria with respect to position 1419 of the *Escherichia coli* 23S ribosomal RNA reference sequence determined by Brosius et al. (1980; Proc. Natl. Acad. Sci. USA; 77: 201–204). A collection of strains of mycobacteria was tested by hybridization with the 23S ribosomal RNA, and enabled the specificity of this probe to be established a posteriori.

The hybridization of the ribosomal RNAs of a target bacteriumwas performed according to the nonradioactive and semi-automated detection method described in French Patent No. 90/07249 and modified for the detection of ribosomal RNA by the addition of a destabilizing agent. A capture probe (34 nucleotides in *M. tuberculosis*, inserted corresponding to the coordinates 1419–1424 of *E. coli*) and an oligonucleotide-enzyme detection conjugate (the oligonucleotide corresponding to the probe defined at the beginning of Example 3) are used. Manipulations were performed in a microtitration plate according to the following protocol.

The ribosomal RNA of the strains was extracted according to the basic protocol for the extraction of RNA from Gram-positive bacteria described in "Current Protocols in Molecular Biology" 1987, Ausubel FM et al., Wiley Interscience, New York. A solution of 1 ng/μl of the capture oligonucleotide whose 5' end has reacted with the reagent Aminolink 2 (Applied Biosystems, Foster City, Calif.) in 3× PBS (0.45M NaCl, 0.15M sodium phosphate, pH 7.0) is applied to a microtitration plate (Nunc 439454). The plate is incubated for 2 h at 37° C. and then washed three times with 300 μl of PBST [1×PBS, Tween 20:0.05% (Merck 822184)]. The Aminolink 2 reagent enables an arm containing a 6-aminohexyl group to be added at the 5' end of the probe. The probe thus coupled to a ligand possessing a polar (primary amine) group and bound passively to the support, achieves an improved signal; see Application FR 91/09057.

The target consisting of 10 μl of extract of total RNAs is mixed with 40 μl of PBS-salmon buffer [3×PBS+salmon sperm DNA 10 μg/ml (Sigma D 9156)]. The mixture is added in the well to 50 μl of a solution of the oligonucleotide-peroxidase conjugate, constituting the detection probe, at a concentration of 0.1 ng/μl of oligonucleotide in PBS-horse buffer [3×PBS+10% horse serum (BioMérieux 55842)]. The plate is incubated for 1 h at 37° C. and then washed with three times 300 µl of PBST buffer. 100 µl of OPD substrate (ortho-phenylenediamine, Cambridge Medical Biotechnology ref/456, in 0.055M citric acid, 0.1M sodium monohydrogen phosphate buffer, pH 4.93) at a concentration of 4 mg/ml, to which 30% hydrogen peroxide diluted to 1/1000 is added immediately before use, are added into each well. After 20 min of reaction, the enzyme activity is blocked with 100 µl of 1N sulfuric acid, and reading is performed on an Axia Microreader apparatus (AXIA: registered trademark) (bioMérieux) at 492 nm.

The target bacteria were, in particular, the following:

50 isolates of *M. tuberculosis*

4 strains of *M. bovis* (including ATCC 19210) and 2 strains of *M. bovis* BCG various other mycobacteria (61 isolates): *M. aviumintracellulare* (including ATCC 35764), *M. asiaticum* (ATCC 25276), *M. chelonae* (ATCC 14472), *M. flavescens, M. fortuitum, M. gastri, M. gordonae, M. kansasii, M. marinum, M. phlei, scrofulaceum, M. simiae, M. smegmatis, M. terrae, M. vaccae, M. xenopi, Nocardia asteroides* (ATCC 3308), *N. brasilensis* (ATCC 19296).

The results obtained show that the combination of probes used is, a posteriori, specific for the tuberculosis complex. It does not display cross-reactions with the nucleic acids, especially the ribosomal RNA, of the other bacterial species. It was checked that the target ribosomal RNAs of the other species are indeed released during the step of lysis, since they react with the combination of capture and detection probes directed against the 16S ribosomal RNA and of eubacterial specificity.

Adaptation of the specific combination to the VIDAS (registered trademark, marketed by the company bioMérieux-VITEK) automated apparatus was performed. The wall of the microplate well is in this case replaced by the SPR (trademark) ("Solid Phase Receptacle"), which is a conical support made from a material sold under the name K resin (butadiene-styrene copolymer) and marketed by the company bioMérieux-VITEK (USA). The various reactants are arranged in a multicuvette bar, and the different steps take place in the SPR which is capable of drawing up and expelling the reactants and which hence acts as a pipette. The sandwich hybridization reaction described in the protocol below proceeds on the inner wall of the cone.

The capture oligonucleotide containing at its 5' end the ligand Aminolink 2 (Applied Biosystems—ref. 400808) at a concentration of 1 ng/µl in a volume of 315 µl of 4×PBS solution (200 mM sodiumphosphate, pH 7.0, 600 mM NaCl) is bound passively to the inner surface of the SPR. After one night at room temperature or 2 hours at 37° C., the cones are washed twice with PBS-Tween solution and then dried under vacuum. The bar contains in cuvettes the reagents needed for the detection, that is to say: 200 µl of a solution at a concentration of 0.1 ng/µl of the oligonucleotide-alkaline phosphatase detection conjugate, twice 600 µl of PBS-Tween washing solution and a cuvette of substrate.

10 µl of the RNA extracted, in the same buffer as for the microplate protocol above, are applied to the first well of the bar.

After a 30-minute incubation of the cone with the mixture of target plus detection probe, the cone is washed twice with PBS-Tween solution. 250 µl of MUP substrate (4-methyl umbelliferyl phosphate) dissolved in diethanolamine buffer are drawn into the cone, and then released into a reading cuvette. The apparatus measures the fluorescent signal expressed in RFU (relative fluorescence units) of the cuvette.

The results obtained with this system are the same as those obtained in microplates.

EXAMPLE 4

Use of a specific probe directed against the 23S rRNA for the identification of *M. xenopi*

The probe beginning at nucleotide 59 and ending at nucleotide 76 of SEQ ID NO 173, or its complementary sequence, in principle specific for the strains of the species *M. xenopi*, was deduced from the alignments of the nucleotide sequences of 23S rRNA in FIGS. 8 and 9. It is present in the insertion of genetic material distinctive to mycobacteria relative to position 1419 of the *Escherichia coli* 23S rRNA reference sequence determined by Brosius et al. A collection of strains of mycobacteria was tested by hybridization with the 23S rRNA, and enabled the specificity of this probe to be established a posterjori.

The hybridization of the rRNAs of a target bacterium was performed according to the method described in Example 3 above for the VIDAS automated apparatus. A capture probe (30 nucleotides in *M. xenopi*, corresponding to the coordinates 81–110 of SEQ ID NO 173) and an oligonucleotide-enzyme detection conjugate, corresponding to the coordinates 59–76 of SEQ ID NO 173, are used.

The target bacteria tested were, in particular, the following:

10 clinical isolates of *M. xenopi* various other mycobacteria (56 isolates), including two strains of *M. bovis* (including ATCC 19210), *M. asiaticum* (ATCC 25276), *M. avium-intracellulare* (including ATCC 35764), *M. chelonae* (ATCC 14472), *M. flavescens, M. fortuitum, M. gastri, M. gordonae, M. kansasii, M. marinum, M. non chromogenicum, M. phlei, M. scrofulaceum, M. simiae, M. smegmatis, M. szulgai, M. terrae, M. vaccae, Nocardia asteroides* (ATCC 3308), *M. brasilensis* (ATCC 19296).

The results obtained show that the combination of probes is specific for the species *M. xenopi*. It does not display cross-reactions with the nucleic acids, especially the rRNA, of the other bacterial species tested. It was checked that the target rRNAs of the other species are indeed released during the step of lysis, since they react with the combination of probes directed against the 16S rRNA and of eubacterial specificity.

EXAMPLE 5

Use of a specific probe directed against the rRNA for the identification of *M. fortuitum*

The probe beginning at nucleotide 6 and ending at nucleotide 22 of SEQ ID NO 117, or its complementary sequence, in principle specific for the strains of the species *M. fortuitum*, was deduced from the alignments of the nucleotide sequences of 23S rRNA in FIG. 10. A collection of strains of mycobacteria was tested by hybridization with the 23S rRNA, and enabled the specificity of this probe to be established a posteriori.

The hybridization of the rRNAs of a target bacterium was performed according to the method described in Example 3 above for the VIDAS automated apparatus. A capture probe (24 nucleotides in *M. fortuitum*, corresponding to the coordinates 1468–1493 of *E. coli*) and an oligonucleotide-enzyme detection conjugate, corresponding to the coordinates 6–22 of SEQ ID NO 117, are used.

The target bacteria tested were, in particular, the following:

8 clinical isolates of *M. fortuitum*
various other mycobacteria (45 isolates), including 2 strains of *M. bovis* (including ATCC 19210), *M. asiaticum* (ATCC 25276), *M. avium-intracellulare* (including ATCC 35764), *M. chelonae* (ATCC 14472), *M. flavescens, M. fortuitum, M. gastri, M. gordonae, M. kansasii, M. marinum, M. non chromogenicum, M. phlei, M. scrofulaceum, M. simiae, M. smegmatis, M. szulgai, M. terrae, M. triviale, M. vaccae, M. xenopi,* *Nocardia asteroides* (ATCC 3308), *M. brasilensis* (ATCC 19296).

The results obtained show that the combination of probes used is specific for the species *M. fortuitum*. It does not display cross-reactions with the nucleic acids, especially the rRNA, of the other bacterial species tested. It was checked that the target rRNAs of the other species are indeed released during the step of lysis, since they react with the combination of probes directed against the 16S rRNA and of eubacterial specificity.

SEQUENCE LISTING ( 1 ) GENERAL INFORMATION:

( i i i ) NUMBER OF SEQUENCES: 178

( 2 ) INFORMATION FOR SEQ ID NO:1:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. TUBERCULOSIS
      ( B ) STRAIN: A 203

( v i i i ) POSITION IN GENOME:
      ( B ) MAP POSITION: 137..179, with respect to the numbering of E. coli ( x i ) SEQUENCE DESCRIPTION: SEQ ID NO:1:

AGUGAUGUCG UGCUACCCGC AUCUGAAUAU AUAGGGUGCG GGAGG    45

( 2 ) INFORMATION FOR SEQ ID NO:2:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. BOVIS BCG
      ( B ) STRAIN: H_P. PASTEUR ( v i i i ) POSITION IN GENOME:
      ( B ) MAP POSITION: 137..179, with respect to the numbering of E. coli ( x i ) SEQUENCE DESCRIPTION: SEQ ID NO:2:

AGUGAUGUCG UGCUACCCGC AUCUGAAUAU AUAGGGUGCG GGAGG    45

( 2 ) INFORMATION FOR SEQ ID NO:3:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. AFRICANUM
      ( B ) STRAIN: CIP 140 030 001

( v i i i ) POSITION IN GENOME:
    ( B ) MAP POSITION: 137..179, with respect to the numbering of
    E. coli ( x i ) SEQUENCE DESCRIPTION: SEQ ID NO:3:

AGUGAUGUCG UGUUACCCGU AUCUGAAUAU AUAGGGUGCG GGAGG     45

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. MARINUM
        ( B ) STRAIN: CIP 140 120 001

( v i i i ) POSITION IN GENOME:
        ( B ) MAP POSITION: 137..179, with respect to the numbering of
        E. coli ( x i ) SEQUENCE DESCRIPTION: SEQ ID NO:4:

AGUGAUGUCG UGUUACCCGC ACCUGAAUAU AUAGGGUGCG GGGG     44

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. VACCAE ( v i i i ) POSITION IN GENOME:
        ( B ) MAP POSITION: 137..179, with respect to the numbering of
        E. coli ( x i ) SEQUENCE DESCRIPTION: SEQ ID NO:5:

AGUGAUGUCG UGUCACCCGG CACUGAAUCU CUCGGGUGCG GGAGGC     46

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. INTRACELLULARE
        ( B ) STRAIN: CIP 140 310 001

( v i i i ) POSITION IN GENOME:
        ( B ) MAP POSITION: 174..179, with respect to the numbering of
        E. coli ( x i ) SEQUENCE DESCRIPTION: SEQ ID NO:6:

CCGCAUCUGA AUAUAUAGGG UGCGGGAGG     29

( 2 ) INFORMATION FOR SEQ ID NO:7:

( i ) SEQUENCE CHARACTERISTICS:

(A) LENGTH: 45 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: M. SCROFULACEUM
(B) STRAIN: CIP 140 220 001

(viii) POSITION IN GENOME:
(B) MAP POSITION: 137..179, with respect to the numbering of E. coli (xi) SEQUENCE DESCRIPTION: SEQ ID NO:7:

AGUGAUGUCG UGUUACCCGC AUCUGAAUAU AUAGGGUUCG GGAGG 45

(2) INFORMATION FOR SEQ ID NO:8:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: M. SZULGAI
(B) STRAIN: A 253

(viii) POSITION IN GENOME:
(B) MAP POSITION: 137..179, with respect to the numbering of E. coli (xi) SEQUENCE DESCRIPTION: SEQ ID NO:8:

AGUGAUGUCG UGUCACCCGG CACUGAAUAC AUAGGUGUCG GGGGG 45

(2) INFORMATION FOR SEQ ID NO:9:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: M. TERRAE
(B) STRAIN: A 255

(viii) POSITION IN GENOME:
(B) MAP POSITION: 137..179, with respect to the numbering of E. coli (xi) SEQUENCE DESCRIPTION: SEQ ID NO:9:

AGUGAUGUCG UGUCACCCGG CACNGAAUAC AUAGGUGUC GGGAGG 46

(2) INFORMATION FOR SEQ ID NO:10:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: M. CHELONAE
(B) STRAIN: A 232

( v i i i ) POSITION IN GENOME:
            ( B ) MAP POSITION: 137..179, with respect to the numbering of
                E. coli ( x i ) SEQUENCE DESCRIPTION: SEQ ID NO:10:

AGUGAUGUCG UGUCACCAGG CGCUGAAUAU AUAGGCGUCU GGGAGG    46

( 2 ) INFORMATION FOR SEQ ID NO:11:

( i ) SEQUENCE CHARACTERISTICS:
            ( A ) LENGTH: 44 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. FORTUITUM
            ( B ) STRAIN: CIP 140 410 001

( v i i i ) POSITION IN GENOME:
            ( B ) MAP POSITION: 137..179, with respect to the numbering of
                E. coli ( x i ) SEQUENCE DESCRIPTION: SEQ ID NO:11:

AGUGAUGUCG UGUCACCCUG CACUGAAUAC AUAGGUGUAG GAGG    44

( 2 ) INFORMATION FOR SEQ ID NO:12:

( i ) SEQUENCE CHARACTERISTICS:
            ( A ) LENGTH: 45 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. PHLEI
            ( B ) STRAIN: A 247

( v i i i ) POSITION IN GENOME:
            ( B ) MAP POSITION: 137..179, with respect to the numbering of
                E. coli ( x i ) SEQUENCE DESCRIPTION: SEQ ID NO:12:

AGUGAUGUCG UGUCACCCAA CGCUGAAUAU AUAGGCGUUG GGGGG    45

( 2 ) INFORMATION FOR SEQ ID NO:13:

( i ) SEQUENCE CHARACTERISTICS:
            ( A ) LENGTH: 44 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. CHITAE
            ( B ) STRAIN: ATCC 19627

( v i i i ) POSITION IN GENOME:
            ( B ) MAP POSITION: 137..179, with respect to the numbering of
                E. coli ( x i ) SEQUENCE DESCRIPTION: SEQ ID NO:13:

AGUGAUGUCG UGUCACCCGU AUCUGAAUUC AUAGUGGCGG GAGG    44

( 2 ) INFORMATION FOR SEQ ID NO:14:

( i ) SEQUENCE CHARACTERISTICS:
  ( A ) LENGTH: 46 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. SMEGMATIS
  ( B ) STRAIN: A 251

( v i i i ) POSITION IN GENOME:
  ( B ) MAP POSITION: 137..179, with respect to the numbering of
        E. coli ( x i ) SEQUENCE DESCRIPTION: SEQ ID NO:14:

AGUGAUGUCG UGUCACCAGG CGCUGAAUAU AUAGGCGUCU GGGGGG    46

( 2 ) INFORMATION FOR SEQ ID NO:15:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. TUBERCULOSIS
    ( B ) STRAIN: A 203

( v i i i ) POSITION IN GENOME:
    ( B ) MAP POSITION: 206..248, with respect to the numbering of
          E. coli ( x i ) SEQUENCE DESCRIPTION: SEQ ID NO:15:

UACCCGUAGG AGGAGAAAAC AAUUGUGAUU CCGCAAGUAG UGG    43

( 2 ) INFORMATION FOR SEQ ID NO:16:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. BOVIS BCG
    ( B ) STRAIN: H_P. PASTEUR ( v i i i ) POSITION IN GENOME:
    ( B ) MAP POSITION: 206..248, with respect to the numbering of
          E. coli ( x i ) SEQUENCE DESCRIPTION: SEQ ID NO:16:

UACCCGUAGG AGGAGAAAAC AAUUGUGAUU CCGCAAGUAG UGG    43

( 2 ) INFORMATION FOR SEQ ID NO:17:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. AFRICANUM
    ( B ) STRAIN: CIP 140 030 001

-continued ( v i i i ) POSITION IN GENOME:
   ( B ) MAP POSITION: 206..248, with respect to the numbering of
    E. coli ( x i ) SEQUENCE DESCRIPTION: SEQ ID NO:17:

UACCCGUAGA GAAAGAAAAC AAUUCUGAUU CCGUCAGUAG UGG     43

( 2 ) INFORMATION FOR SEQ ID NO:18:

( i ) SEQUENCE CHARACTERISTICS:
  ( A ) LENGTH: 43 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. MARINUM
  ( B ) STRAIN: CIP 140 120 001

( v i i i ) POSITION IN GENOME:
  ( B ) MAP POSITION: 206..248, with respect to the numbering of
   E. coli ( x i ) SEQUENCE DESCRIPTION: SEQ ID NO:18:

UACCCGUAGG AAAAGAAAAC AAUUGUGAUU CCGUAAGUAG UGG     43

( 2 ) INFORMATION FOR SEQ ID NO:19:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. VACCAE ( v i i i ) POSITION IN GENOME:
  ( B ) MAP POSITION: 206..215, with respect to the numbering of
   E. coli ( x i ) SEQUENCE DESCRIPTION: SEQ ID NO:19:

UCCCCGNCGG     10

( 2 ) INFORMATION FOR SEQ ID NO:20:

( i ) SEQUENCE CHARACTERISTICS:
  ( A ) LENGTH: 43 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. INTRACELLULARE
  ( B ) STRAIN: CIP 140 310 001

( v i i i ) POSITION IN GENOME:
  ( B ) MAP POSITION: 206..248, with respect to the numbering of
   E. coli ( x i ) SEQUENCE DESCRIPTION: SEQ ID NO:20:

UACCCGUAGG AGAAGAAAAC AAUUGUGAUU CCGUAAGUAG UGG     43

( 2 ) INFORMATION FOR SEQ ID NO:21:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. SCROFULACEUM
    ( B ) STRAIN: CIP 140 220 001

( v i i i ) POSITION IN GENOME:
    ( B ) MAP POSITION: 206..248, with respect to the numbering of
        E. coli ( x i ) SEQUENCE DESCRIPTION: SEQ ID NO:21:

UACCCGUAGG AGAAGAAAAC AAUUGUGAUU CCGUUAGUAG UGG    43

( 2 ) INFORMATION FOR SEQ ID NO:22:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. SZULGAI
    ( B ) STRAIN: A 253

( v i i i ) POSITION IN GENOME:
    ( B ) MAP POSITION: 206..248, with respect to the numbering of
        E. coli ( x i ) SEQUENCE DESCRIPTION: SEQ ID NO:22:

UACCCGUAGA AGAGAAAACA AAGUGAUUC CGUGAGUAGU GG    42

( 2 ) INFORMATION FOR SEQ ID NO:23:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. TERRAE
    ( B ) STRAIN: A 255

( v i i i ) POSITION IN GENOME:
    ( B ) MAP POSITION: 206..248, with respect to the numbering of
        E. coli ( x i ) SEQUENCE DESCRIPTION: SEQ ID NO:23:

UACCCGUAGG AGGAGAAAAC ANANGUGAUU CCGUGAGUAG UGG    43

( 2 ) INFORMATION FOR SEQ ID NO:24:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. CHELONAE
    ( B ) STRAIN: A 232

(viii) POSITION IN GENOME:
    (B) MAP POSITION: 206..248, with respect to the numbering of
        E. coli (xi) SEQUENCE DESCRIPTION: SEQ ID NO:24:

UACCCGUAGA AGAGAAAACA AAAUGUGAUU CCGUGAGUAG UGG    43

(2) INFORMATION FOR SEQ ID NO:25:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. FORTUITUM
        (B) STRAIN: CIP 140 410 001

(viii) POSITION IN GENOME:
        (B) MAP POSITION: 206..248, with respect to the numbering of
            E. coli (xi) SEQUENCE DESCRIPTION: SEQ ID NO:25:

UACCCGUAGG AAGAGAAAAC AAAAUGUGAU UCCGUGAGUA GUGG    44

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. PHLEI
        (B) STRAIN: A 247

(viii) POSITION IN GENOME:
        (B) MAP POSITION: 206..248, with respect to the numbering of
            E. coli (xi) SEQUENCE DESCRIPTION: SEQ ID NO:26:

UACCCGUAGA AGAGAAAACA AUUGUGAUUC CGUGAGUAGU GG    42

(2) INFORMATION FOR SEQ ID NO:27:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. CHITAE
        (B) STRAIN: ATCC 19627

(viii) POSITION IN GENOME:
        (B) MAP POSITION: 206..248, with respect to the numbering of
            E. coli (xi) SEQUENCE DESCRIPTION: SEQ ID NO:27:

UACCCGUAGG AAGAGAAAAC AAUUGUGAUU CCGUGAGUAG UGG    43

(2) INFORMATION FOR SEQ ID NO:28:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: M. SMEGMATIS
( B ) STRAIN: A 251

( v i i i ) POSITION IN GENOME:
( B ) MAP POSITION: 206..248, with respect to the numbering of E. coli ( x i ) SEQUENCE DESCRIPTION: SEQ ID NO:28:

UACCCGUAGA AAGAGAAAAN CAAAUGUGAU UCCGUGAGUA GUGG    44

( 2 ) INFORMATION FOR SEQ ID NO:29:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: M. TUBERCULOSIS
( B ) STRAIN: A 203

( v i i i ) POSITION IN GENOME:
( B ) MAP POSITION: 269..289, with respect to the numbering of E. coli ( x i ) SEQUENCE DESCRIPTION: SEQ ID NO:29:

UAAACCGCAC GCAUGGGUAA CCGGGUAGGG GUUGU    35

( 2 ) INFORMATION FOR SEQ ID NO:30:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: M. BOVIS BCG
( B ) STRAIN: H_P. PASTEUR ( v i i i ) POSITION IN GENOME:
( B ) MAP POSITION: 269..289, with respect to the numbering of E. coli ( x i ) SEQUENCE DESCRIPTION: SEQ ID NO:30:

UAAACCGCAC GCAUGGGUAA CCGGGUAGGG GUUGU    35

( 2 ) INFORMATION FOR SEQ ID NO:31:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: M. AFRICANUM

（B）STRAIN: CIP 140 030 001

(viii) POSITION IN GENOME:
(B) MAP POSITION: 269..289, with respect to the numbering of
E. coli (xi) SEQUENCE DESCRIPTION: SEQ ID NO:31:

UAAACCGCAU GCAUGGACAA CCGGGUAGGG GUUGU                                   35

(2) INFORMATION FOR SEQ ID NO:32:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: M. MARINUM
(B) STRAIN: CIP 140 120 001

(viii) POSITION IN GENOME:
(B) MAP POSITION: 269..289, with respect to the numbering of
E. coli (xi) SEQUENCE DESCRIPTION: SEQ ID NO:32:

UAAACCGCAC GCAUGUUUAA CCGGGUAGGG GUUGU                                   35

(2) INFORMATION FOR SEQ ID NO:33:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: M. INTRACELLULARE
(B) STRAIN: CIP 140 310 001

(viii) POSITION IN GENOME:
(B) MAP POSITION: 269..289, with respect to the numbering of
E. coli (xi) SEQUENCE DESCRIPTION: SEQ ID NO:33:

UAAACCGCAC GCAUGUGAUA CCGGGUAGGG GUUGU                                   35

(2) INFORMATION FOR SEQ ID NO:34:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: M. SCROFULACEUM
(B) STRAIN: CIP 140 220 001

(viii) POSITION IN GENOME:
(B) MAP POSITION: 269..289, with respect to the numbering of
E. coli (xi) SEQUENCE DESCRIPTION: SEQ ID NO:34:

UAAACCGCAU GCAUGGAUAA CCGGGUAGGG GUUGU                                   35

( 2 ) INFORMATION FOR SEQ ID NO:35:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SZULGAI
        ( B ) STRAIN: A 253

( v i i i ) POSITION IN GENOME:
        ( B ) MAP POSITION: 269..289, with respect to the numbering of
        E. coli ( x i ) SEQUENCE DESCRIPTION: SEQ ID NO:35:

UAAACCGUGC ACAUGUGAUA CCCGGCAGGG GUUGU                           35

( 2 ) INFORMATION FOR SEQ ID NO:36:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. TERRAE
        ( B ) STRAIN: A 255

( v i i i ) POSITION IN GENOME:
        ( B ) MAP POSITION: 269..289, with respect to the numbering of
        E. coli ( x i ) SEQUENCE DESCRIPTION: SEQ ID NO:36:

UAAACCGUGC ACAUGUGAUA CCCGGCAGGG GUUGU                           35

( 2 ) INFORMATION FOR SEQ ID NO:37:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. CHELONAE
        ( B ) STRAIN: A 232

( v i i i ) POSITION IN GENOME:
        ( B ) MAP POSITION: 269..289, with respect to the numbering of
        E. coli ( x i ) SEQUENCE DESCRIPTION: SEQ ID NO:37:

UAAACCGAUG CAUGUGAUAC CGGG                                    24

( 2 ) INFORMATION FOR SEQ ID NO:38:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:

(A) ORGANISM: M. FORTUITUM
                (B) STRAIN: CIP 140 410 001

(viii) POSITION IN GENOME:
                (B) MAP POSITION: 269..289, with respect to the numbering of
                    E. coli (xi) SEQUENCE DESCRIPTION: SEQ ID NO:38:

UAAACCGUAU GCAUGUGAUC CGGGUAGGGG UUGU                    34

(2) INFORMATION FOR SEQ ID NO:39:

(i) SEQUENCE CHARACTERISTICS:
                (A) LENGTH: 35 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. PHLEI
                (B) STRAIN: A 247

(viii) POSITION IN GENOME:
                (B) MAP POSITION: 269..289, with respect to the numbering of
                    E. coli (xi) SEQUENCE DESCRIPTION: SEQ ID NO:39:

UAAACCGCGU GCAUGUGAUA CCCGGCGGGG GUUGU                   35

(2) INFORMATION FOR SEQ ID NO:40:

(i) SEQUENCE CHARACTERISTICS:
                (A) LENGTH: 35 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. CHITAE
                (B) STRAIN: ATCC 19627

(viii) POSITION IN GENOME:
                (B) MAP POSITION: 269..289, with respect to the numbering of
                    E. coli (xi) SEQUENCE DESCRIPTION: SEQ ID NO:40:

UAAACCGUGU GCAUGUGAUA CCCGGCGGGG GUUGU                   35

(2) INFORMATION FOR SEQ ID NO:41:

(i) SEQUENCE CHARACTERISTICS:
                (A) LENGTH: 35 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. SMEGMATIS
                (B) STRAIN: A 251

(viii) POSITION IN GENOME:
                (B) MAP POSITION: 269..289, with respect to the numbering of
                    E. coli (xi) SEQUENCE DESCRIPTION: SEQ ID NO:41:

GAAACCGUAU GCAUGUGAUA CCGGNUAGGG GUUGU                   35

( 2 ) INFORMATION FOR SEQ ID NO:42:

( i ) SEQUENCE CHARACTERISTICS:
      ( A ) LENGTH: 58 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. TUBERCULOSIS
      ( B ) STRAIN: A 203

( v i i i ) POSITION IN GENOME:
      ( B ) MAP POSITION: 289..290, with respect to the numbering of
            E. coli ( x i ) SEQUENCE DESCRIPTION: SEQ ID NO:42:

GUUGUGGGAN GAUAUGUCUC AGCGCUACCC GGCUGAGAGG CAGUCAGAAA GUGUCGUG    58

( 2 ) INFORMATION FOR SEQ ID NO:43:

( i ) SEQUENCE CHARACTERISTICS:
      ( A ) LENGTH: 58 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. BOVIS BCG
      ( B ) STRAIN: H_P. PASTEUR ( v i i i ) POSITION IN GENOME:
      ( B ) MAP POSITION: 289..290, with respect to the numbering of
            E. coli ( x i ) SEQUENCE DESCRIPTION: SEQ ID NO:43:

GUUGUGGGAG GAUAUGUCUC AGCGCUACCC GGCUGAGAGG CAGUCAGAAA GUGUCGUG    58

( 2 ) INFORMATION FOR SEQ ID NO:44:

( i ) SEQUENCE CHARACTERISTICS:
      ( A ) LENGTH: 59 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. AFRICANUM
      ( B ) STRAIN: CIP 140 030 001

( v i i i ) POSITION IN GENOME:
      ( B ) MAP POSITION: 289..290, with respect to the numbering of
            E. coli ( x i ) SEQUENCE DESCRIPTION: SEQ ID NO:44:

GUUGUGGGAU UGAUAUGUCU CAGCUCUACC UGGCUGAGGG GUAGUCAGAA AGUGUCGUG    59

( 2 ) INFORMATION FOR SEQ ID NO:45:

( i ) SEQUENCE CHARACTERISTICS:
      ( A ) LENGTH: 59 base pairs
      ( B ) TYPE: nucleic acid
      ( C ) STRANDEDNESS: single
      ( D ) TOPOLOGY: linear ( i i ) MOLECULE TYPE: rRNA -continued ( v i ) ORIGINAL SOURCE:
        ( A ) ORGANISM: M. MARINUM
        ( B ) STRAIN: CIP 140 120 001

( v i i i ) POSITION IN GENOME:
        ( B ) MAP POSITION: 289..290, with respect to the numbering of
        E. coli ( x i ) SEQUENCE DESCRIPTION: SEQ ID NO:45:

GUUGUGGAA UGAUAUGUCU CAGCUCUACC UGGCUGAGAG GCAGUCAGAA AGUGUCGCA 59

( 2 ) INFORMATION FOR SEQ ID NO:46:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. INTRACELLULARE
        ( B ) STRAIN: CIP 140 310 001

( v i i i ) POSITION IN GENOME:
        ( B ) MAP POSITION: 289..290, with respect to the numbering of
        E. coli ( x i ) SEQUENCE DESCRIPTION: SEQ ID NO:46:

GUUGUGGAG GAUACAUCUC AGCUCUACCU GGCUGAGGGG UAGUCAGAAA GUGUCGUG 58

( 2 ) INFORMATION FOR SEQ ID NO:47:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SCROFULACEUM
        ( B ) STRAIN: CIP 140 220 001

( v i i i ) POSITION IN GENOME:
        ( B ) MAP POSITION: 289..290, with respect to the numbering of
        E. coli ( x i ) SEQUENCE DESCRIPTION: SEQ ID NO:47:

GUUGUGGAU UGAUAUGUCU CAGCUCUACC UGGCUGAGGG GUAGUCAGAA AGUGUCGUG 59

( 2 ) INFORMATION FOR SEQ ID NO:48:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SZULGAI
        ( B ) STRAIN: A 253

( v i i i ) POSITION IN GENOME:
        ( B ) MAP POSITION: 289..290, with respect to the numbering of
        E. coli ( x i ) SEQUENCE DESCRIPTION: SEQ ID NO:48:

GUUGUGGUG CAUCAGUCCU GGAUCUGCCG GUCUGGGCUG CAGUGAGAAA AGCUCGUG 58

( 2 ) INFORMATION FOR SEQ ID NO:49:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. TERRAE
        ( B ) STRAIN: A 255

( v i i i ) POSITION IN GENOME:
        ( B ) MAP POSITION: 289..290, with respect to the numbering of
            E. coli ( x i ) SEQUENCE DESCRIPTION: SEQ ID NO:49:

GUUGUGGGU GCAUCAGUCC UGGAUCUGCC GGUCUGGGCU CGAGUGAGAA AAGCUCGUG    59

( 2 ) INFORMATION FOR SEQ ID NO:50:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. FORTUITUM
        ( B ) STRAIN: CIP 140 410 001

( v i i i ) POSITION IN GENOME:
        ( B ) MAP POSITION: 289..290, with respect to the numbering of
            E. coli ( x i ) SEQUENCE DESCRIPTION: SEQ ID NO:50:

GUUGUGGGAC CUGUUUUUCC AGUUCUACCU GGCUGGAGGG UAGUGAGAAA AUGUCGUG    58

( 2 ) INFORMATION FOR SEQ ID NO:51:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. PHLEI
        ( B ) STRAIN: A 247

( v i i i ) POSITION IN GENOME:
        ( B ) MAP POSITION: 289..290, with respect to the numbering of
            E. coli ( x i ) SEQUENCE DESCRIPTION: SEQ ID NO:51:

GUUGUGGGC CUGUGUUCCA UCGUCCGCCG GCGAUGGCAG UAGUGAUAAA AGCAGUGU    58

( 2 ) INFORMATION FOR SEQ ID NO:52:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. CHITAE
        ( B ) STRAIN: ATCC 19627

( v i i i ) POSITION IN GENOME:
        ( B ) MAP POSITION: 289..290, with respect to the numbering of
              E. coli ( x i ) SEQUENCE DESCRIPTION: SEQ ID NO:52:

GUUGUGGGCG UUUCUUCUCA GGUCCUGCGG CCUGGGCGAC AGUCAGAAAG UGUGUGU    57

( 2 ) INFORMATION FOR SEQ ID NO:53:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SMEGMATIS
        ( B ) STRAIN: A 251

( v i i i ) POSITION IN GENOME:
        ( B ) MAP POSITION: 289..290, with respect to the numbering of
              E. coli ( x i ) SEQUENCE DESCRIPTION: SEQ ID NO:53:

GUUGUGGGNC CUAUCUUUCC GGCUCUACCU GGCUGGAGGG UAGUGAGAAA UGUUGUG    57

( 2 ) INFORMATION FOR SEQ ID NO:54:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. TUBERCULOSIS
        ( B ) STRAIN: A 203

( v i i i ) POSITION IN GENOME:
        ( B ) MAP POSITION: 341..372, with respect to the numbering of
              E. coli ( x i ) SEQUENCE DESCRIPTION: SEQ ID NO:54:

CGCGAAAACN CCGGCACCUG CCUAGUAUCA AUUCCGAG    39

( 2 ) INFORMATION FOR SEQ ID NO:55:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. BOVIS BCG
        ( B ) STRAIN: H_P. PASTEUR ( v i i i ) POSITION IN GENOME:
        ( B ) MAP POSITION: 341..372, with respect to the numbering of
              E. coli ( x i ) SEQUENCE DESCRIPTION: SEQ ID NO:55:

```
CGCGAAAACC CGGCACCUGC CUAGUAUCAA UUCCCGAG                    38
```

(2) INFORMATION FOR SEQ ID NO:56:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. AFRICANUM
        (B) STRAIN: CIP 140 030 001

(viii) POSITION IN GENOME:
        (B) MAP POSITION: 341..372, with respect to the numbering of E. coli (xi) SEQUENCE DESCRIPTION: SEQ ID NO:56:

```
CGCGAAAACC CGGCACCUGC UUAUAUCAAC ACCCGAG                     37
```

(2) INFORMATION FOR SEQ ID NO:57:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. MARINUM
        (B) STRAIN: CIP 140 120 001

(viii) POSITION IN GENOME:
        (B) MAP POSITION: 341..372, with respect to the numbering of E. coli (xi) SEQUENCE DESCRIPTION: SEQ ID NO:57:

```
CGUGAAAACC CGGCACCUGC CUAGUAUCAA CUCCCGAG                    38
```

(2) INFORMATION FOR SEQ ID NO:58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. VACCAE (viii) POSITION IN GENOME:
        (B) MAP POSITION: 361..372, with respect to the numbering of E. coli (xi) SEQUENCE DESCRIPTION: SEQ ID NO:58:

```
UAUGUGUANN UCCCGAG                                           17
```

(2) INFORMATION FOR SEQ ID NO:59:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
                (A) ORGANISM: M. INTRACELLULARE
                (B) STRAIN: CIP 140 310 001

(viii) POSITION IN GENOME:
                (B) MAP POSITION: 341..372, with respect to the numbering of
                    E. coli (xi) SEQUENCE DESCRIPTION: SEQ ID NO:59:

CGCGAAAACC CGUCACCUAC CUUGUAUCAN UUCCCGAG         38

(2) INFORMATION FOR SEQ ID NO:60:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. SCROFULACEUM
                (B) STRAIN: CIP 140 220 001

(viii) POSITION IN GENOME:
                (B) MAP POSITION: 341..372, with respect to the numbering of
                    E. coli (xi) SEQUENCE DESCRIPTION: SEQ ID NO:60:

CGCGAAAACC CGGCACCUAC CUUGUAUCAA CACCCGAG         38

(2) INFORMATION FOR SEQ ID NO:61:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. SZULGAI
                (B) STRAIN: A 253

(viii) POSITION IN GENOME:
                (B) MAP POSITION: 341..372, with respect to the numbering of
                    E. coli (xi) SEQUENCE DESCRIPTION: SEQ ID NO:61:

GGUGAAAACA CAGUGCUCUG UAGUGAUGUG UCCCCGAG         38

(2) INFORMATION FOR SEQ ID NO:62:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. TERRAE
                (B) STRAIN: A 255

(viii) POSITION IN GENOME:
                (B) MAP POSITION: 341..372, with respect to the numbering of
                    E. coli (xi) SEQUENCE DESCRIPTION: SEQ ID NO:62:

GGUGAAAACA CCGUGCUCUG UAGUGAUGUG UCCCCGAG                           38

( 2 ) INFORMATION FOR SEQ ID NO:63:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. CHELONAE
    ( B ) STRAIN: A 232

( v i i i ) POSITION IN GENOME:
    ( B ) MAP POSITION: 341..372, with respect to the numbering of
     E. coli ( x i ) SEQUENCE DESCRIPTION: SEQ ID NO:63:

CGUGAAAACC CGACGUCUGU CUUGAUGGUG UUCCCGAG                           38

( 2 ) INFORMATION FOR SEQ ID NO:64:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. FORTUITUM
    ( B ) STRAIN: CIP 140 410 001

( v i i i ) POSITION IN GENOME:
    ( B ) MAP POSITION: 341..372, with respect to the numbering of
     E. coli ( x i ) SEQUENCE DESCRIPTION: SEQ ID NO:64:

CGUGAAAACC UGACAUCUAC CAAGAACGGU GUUCCCGAG                          39

( 2 ) INFORMATION FOR SEQ ID NO:65:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. PHLEI
    ( B ) STRAIN: A 247

( v i i i ) POSITION IN GENOME:
    ( B ) MAP POSITION: 341..372, with respect to the numbering of
     E. coli ( x i ) SEQUENCE DESCRIPTION: SEQ ID NO:65:

ACCGAAAACA UGCUGCCUGC UGUCACAGGU UCCCGAG                            37

( 2 ) INFORMATION FOR SEQ ID NO:66:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear (i i) MOLECULE TYPE: rRNA (v i) ORIGINAL SOURCE:
 (A) ORGANISM: M. CHITAE
 (B) STRAIN: ATCC 19627

(v i i i) POSITION IN GENOME:
 (B) MAP POSITION: 341..372, with respect to the numbering of
  E. coli (x i) SEQUENCE DESCRIPTION: SEQ ID NO:66:

GGCGAAAACA UGCACUCUGU UGUGGAAUGU UCCCGAG    37

(2) INFORMATION FOR SEQ ID NO:67:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (i i) MOLECULE TYPE: rRNA (v i) ORIGINAL SOURCE:
 (A) ORGANISM: M. SMEGMATIS
 (B) STRAIN: A 251

(v i i i) POSITION IN GENOME:
 (B) MAP POSITION: 341..372, with respect to the numbering of
  E. coli (x i) SEQUENCE DESCRIPTION: SEQ ID NO:67:

CGUGAAAACC CGACGUCUGU CUUGAUGGUG UUCCCGAG    38

(2) INFORMATION FOR SEQ ID NO:68:

(i) SEQUENCE CHARACTERISTICS:
  (A) LENGTH: 35 base pairs
  (B) TYPE: nucleic acid
  (C) STRANDEDNESS: single
  (D) TOPOLOGY: linear (i i) MOLECULE TYPE: rRNA (v i) ORIGINAL SOURCE:
 (A) ORGANISM: M. TUBERCULOSIS
 (B) STRAIN: A 203

(v i i i) POSITION IN GENOME:
 (B) MAP POSITION: 645..661, with respect to the numbering of
  E. coli (x i) SEQUENCE DESCRIPTION: SEQ ID NO:68:

UAGGGCGAUC CCAUACGCGC GUGUGAAUAG UGGCG    35

(2) INFORMATION FOR SEQ ID NO:69:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (i i) MOLECULE TYPE: rRNA (v i) ORIGINAL SOURCE:
 (A) ORGANISM: M. AFRICANUM
 (B) STRAIN: CIP 140 030 001

(v i i i) POSITION IN GENOME:
 (B) MAP POSITION: 645..661, with respect to the numbering of
  E. coli (x i) SEQUENCE DESCRIPTION: SEQ ID NO:69:

```
UAGGGCGAUC CCUUUGGGGG UGUAGUGGCG                                    30
```

( 2 ) INFORMATION FOR SEQ ID NO:70:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. MARINUM
        ( B ) STRAIN: CIP 140 120 001

( v i i i ) POSITION IN GENOME:
        ( B ) MAP POSITION: 645..661, with respect to the numbering of
            E. coli ( x i ) SEQUENCE DESCRIPTION: SEQ ID NO:70:

```
UAGGGCGUAU CCCGUAAGGG GUGUAGUGGC G                                  31
```

( 2 ) INFORMATION FOR SEQ ID NO:71:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. INTRACELLULARE
        ( B ) STRAIN: CIP 140 310 001

( v i i i ) POSITION IN GENOME:
        ( B ) MAP POSITION: 645..661, with respect to the numbering of
            E. coli ( x i ) SEQUENCE DESCRIPTION: SEQ ID NO:71:

```
UAGGGCGAUC CCUUUGGGUG UAGUGGCG                                      28
```

( 2 ) INFORMATION FOR SEQ ID NO:72:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SCROFULACEUM
        ( B ) STRAIN: CIP 140 220 001

( v i i i ) POSITION IN GENOME:
        ( B ) MAP POSITION: 645..661, with respect to the numbering of
            E. coli ( x i ) SEQUENCE DESCRIPTION: SEQ ID NO:72:

```
UAGGGCGCAU CCCUUUGGUG UAGUGGCG                                      28
```

( 2 ) INFORMATION FOR SEQ ID NO:73:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
    ( A ) ORGANISM: M. SZULGAI
    ( B ) STRAIN: A 253

( v i i i ) POSITION IN GENOME:
    ( B ) MAP POSITION: 645..661, with respect to the numbering of
    E. coli ( x i ) SEQUENCE DESCRIPTION: SEQ ID NO:73:

UAGGGCGUAU CCACACAACA GUGUGUGGNG UAGUGGCG    38

( 2 ) INFORMATION FOR SEQ ID NO:74:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. TERRAE
        ( B ) STRAIN: A 255

( v i i i ) POSITION IN GENOME:
        ( B ) MAP POSITION: 645..661, with respect to the numbering of
        E. coli ( x i ) SEQUENCE DESCRIPTION: SEQ ID NO:74:

UAGGGCGUAU CCACACAACA GUGUGUGGUG UAGUGGCG    38

( 2 ) INFORMATION FOR SEQ ID NO:75:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. CHELONAE
        ( B ) STRAIN: A 232

( v i i i ) POSITION IN GENOME:
        ( B ) MAP POSITION: 645..661, with respect to the numbering of
        E. coli ( x i ) SEQUENCE DESCRIPTION: SEQ ID NO:75:

UAGGGCGUAU CCACACAAGA GUGUGUGGUG UAGUGGCG    38

( 2 ) INFORMATION FOR SEQ ID NO:76:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. FORTUITUM
        ( B ) STRAIN: CIP 140 410 001

( v i i i ) POSITION IN GENOME:
        ( B ) MAP POSITION: 645..661, with respect to the numbering of
        E. coli ( x i ) SEQUENCE DESCRIPTION: SEQ ID NO:76:

UAGGGCGUAU CCGCACAGUA GUGUGUGGUG UAGUGGCG    38

( 2 ) INFORMATION FOR SEQ ID NO:77:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. PHLEI
        ( B ) STRAIN: A 247

( v i i i ) POSITION IN GENOME:
        ( B ) MAP POSITION: 645..661, with respect to the numbering of
            E. coli ( x i ) SEQUENCE DESCRIPTION: SEQ ID NO:77:

UAGGGCGUAU CCAUACGCUA GUUGGUGUUG GUGUAGUGGC G    41

( 2 ) INFORMATION FOR SEQ ID NO:78:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. CHITAE
        ( B ) STRAIN: ATCC 19627

( v i i i ) POSITION IN GENOME:
        ( B ) MAP POSITION: 645..661, with respect to the numbering of
            E. coli ( x i ) SEQUENCE DESCRIPTION: SEQ ID NO:78:

UAGGGCGUAU CCAGUGAGGC GUGUAGUGGC G    31

( 2 ) INFORMATION FOR SEQ ID NO:79:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SMEGMATIS
        ( B ) STRAIN: A 251

( v i i i ) POSITION IN GENOME:
        ( B ) MAP POSITION: 645..661, with respect to the numbering of
            E. coli ( x i ) SEQUENCE DESCRIPTION: SEQ ID NO:79:

UAGGGCGUAU CCACACAAGA GUGUGUGGUG UAGUGGCG    38

( 2 ) INFORMATION FOR SEQ ID NO:80:

( i ) SEQUENCE CHARACTERISTICS:
        ( A ) LENGTH: 42 base pairs
        ( B ) TYPE: nucleic acid
        ( C ) STRANDEDNESS: single (D) TOPOLOGY: linear (ii) MOLECULE TYPE: rRNA (vi) ORIGINAL SOURCE:
            (A) ORGANISM: M. TUBERCULOSIS
            (B) STRAIN: A 203

(viii) POSITION IN GENOME:
            (B) MAP POSITION: 1201..1242, with respect to the numbering of
                E. coli (xi) SEQUENCE DESCRIPTION: SEQ ID NO:80:

CCUCAUUCAG CGAAGCCACC GGGUGACCGG UGGUGGAGGG UG            42

(2) INFORMATION FOR SEQ ID NO:81:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: rRNA (vi) ORIGINAL SOURCE:
            (A) ORGANISM: M. BOVIS BCG
            (B) STRAIN: H_P. PASTEUR (viii) POSITION IN GENOME:
            (B) MAP POSITION: 1201..1242, with respect to the numbering of
                E. coli (xi) SEQUENCE DESCRIPTION: SEQ ID NO:81:

CCUCAUUCAG CGAAGCACCG AGUGACCGGU GGUGGAGGGU G            41

(2) INFORMATION FOR SEQ ID NO:82:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: rRNA (vi) ORIGINAL SOURCE:
            (A) ORGANISM: M. AFRICANUM
            (B) STRAIN: CIP 140 030 001

(viii) POSITION IN GENOME:
            (B) MAP POSITION: 1201..1242, with respect to the numbering of
                E. coli (xi) SEQUENCE DESCRIPTION: SEQ ID NO:82:

CCCCAUUCAG CGAAGCCUCC GGGUGACCGG UGGUGGAGGG UG            42

(2) INFORMATION FOR SEQ ID NO:83:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: rRNA (vi) ORIGINAL SOURCE:
            (A) ORGANISM: M. MARINUM
            (B) STRAIN: CIP 140 120 001

(viii) POSITION IN GENOME:
            (B) MAP POSITION: 1201..1262, with respect to the numbering of
                E. coli ( x i ) SEQUENCE DESCRIPTION: SEQ ID NO:83:

CCUCAUUCAG CGAAGCUGCC GGGUAACCGU GGUGGAGGAU G 41

( 2 ) INFORMATION FOR SEQ ID NO:84:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. VACCAE ( v i i i ) POSITION IN GENOME:
        ( B ) MAP POSITION: 1201..1262, with respect to the numbering of
            E. coli ( x i ) SEQUENCE DESCRIPTION: SEQ ID NO:84:

CUGCAUCCGG UGAAGCAGCA GAGUGAUCUA GCUGUGGAGG GUC 43

( 2 ) INFORMATION FOR SEQ ID NO:85:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. INTRACELLULARE
        ( B ) STRAIN: CIP 140 310 001

( v i i i ) POSITION IN GENOME:
        ( B ) MAP POSITION: 1201..1242, with respect to the numbering of
            E. coli ( x i ) SEQUENCE DESCRIPTION: SEQ ID NO:85:

CCUCAUUCAG CGAAGCCUCC GGGUGACCGG UGGUGGAGGG UG 42

( 2 ) INFORMATION FOR SEQ ID NO:86:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SCROFULACEUM
        ( B ) STRAIN: CIP 140 220 001

( v i i i ) POSITION IN GENOME:
        ( B ) MAP POSITION: 1201..1242, with respect to the numbering of
            E. coli ( x i ) SEQUENCE DESCRIPTION: SEQ ID NO:86:

CCCCAUGCAG CGAAGCUACC GGGUAACCGG UGGUGGAGUU UG 42

( 2 ) INFORMATION FOR SEQ ID NO:87:

( i ) SEQUENCE CHARACTERISTICS:
        ( A ) LENGTH: 44 base pairs
        ( B ) TYPE: nucleic acid
        ( C ) STRANDEDNESS: single ( D ) TOPOLOGY: linear ( i i ) MOLECULE TYPE: rRNA ( v i ) ORIGINAL SOURCE:
            ( A ) ORGANISM: M. SZULGAI
            ( B ) STRAIN: A 253

( v i i i ) POSITION IN GENOME:
            ( B ) MAP POSITION: 1201..1242, with respect to the numbering of
                E. coli ( x i ) SEQUENCE DESCRIPTION: SEQ ID NO:87:

CUGCAUCCGG UGAAGCAGCA GAGUGAUCUA GCUGUGGGAG GGUG          4 4

( 2 ) INFORMATION FOR SEQ ID NO:88:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. TERRAE
            ( B ) STRAIN: A 255

( v i i i ) POSITION IN GENOME:
            ( B ) MAP POSITION: 1201..1242, with respect to the numbering of
                E. coli ( x i ) SEQUENCE DESCRIPTION: SEQ ID NO:88:

CUGCAUCCGG UGAAGCAGCA GAGUGAUCUA GCUGUGGAGG GUG          4 3

( 2 ) INFORMATION FOR SEQ ID NO:89:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. CHELONAE
            ( B ) STRAIN: A 232

( v i i i ) POSITION IN GENOME:
            ( B ) MAP POSITION: 1201..1242, with respect to the numbering of
                E. coli ( x i ) SEQUENCE DESCRIPTION: SEQ ID NO:89:

CUGCAUCCGG UGAAGCCGCC GAGUGAUCGA GUGGUGGAGG GUG          4 3

( 2 ) INFORMATION FOR SEQ ID NO:90:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. FORTUITUM
            ( B ) STRAIN: CIP 140 410 001

( v i i i ) POSITION IN GENOME:
            ( B ) MAP POSITION: 1201..1242, with respect to the numbering of
                E. coli (x i) SEQUENCE DESCRIPTION: SEQ ID NO:90:

CAGCAUCCGG UGAAGCAGCA GAGUGAUCUA GCUGUGGAGG GUG          43

(2) INFORMATION FOR SEQ ID NO:91:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: M. PHLEI
        (B) STRAIN: A 247

(v i i i) POSITION IN GENOME:
        (B) MAP POSITION: 1201..1242, with respect to the numbering of
            E. coli (x i) SEQUENCE DESCRIPTION: SEQ ID NO:91:

CAGCAUCCGG UGAAGCAGCA GAGUGAUCUA GCUGUGGAGG GUG          43

(2) INFORMATION FOR SEQ ID NO:92:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: M. CHITAE
        (B) STRAIN: ATCC 19627

(v i i i) POSITION IN GENOME:
        (B) MAP POSITION: 1201..1242, with respect to the numbering of
            E. coli (x i) SEQUENCE DESCRIPTION: SEQ ID NO:92:

CUGCAUCCAG UGAAGCAGCC GGGUGACCGU GUUGUGGAGG GUG          43

(2) INFORMATION FOR SEQ ID NO:93:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: M. SMEGMATIS
        (B) STRAIN: A 251

(v i i i) POSITION IN GENOME:
        (B) MAP POSITION: 1201..1242, with respect to the numbering of
            E. coli (x i) SEQUENCE DESCRIPTION: SEQ ID NO:93:

CUGCAUCCGG UGAAGCCGCC GAGUGAUCGA GUGGUGGAGG GUG          43

(2) INFORMATION FOR SEQ ID NO:94:

(i) SEQUENCE CHARACTERISTICS:
        (A) LENGTH: 117 base pairs
        (B) TYPE: nucleic acid (C) STRANDEDNESS: single
        (D) TOPOLOGY: linear (ii) MOLECULE TYPE: rRNA (vi) ORIGINAL SOURCE:
        (A) ORGANISM: M. TUBERCULOSIS
        (B) STRAIN: A 203

(viii) POSITION IN GENOME:
        (B) MAP POSITION: 1409..1420, with respect to the numbering of
            E. coli (xi) SEQUENCE DESCRIPTION: SEQ ID NO:94:

GUGUGGAGCC GUGAUGAUGA AUCACCGGUA CUAACCACCC AAAACCGAUC GAUCGACCUU    60

CCUUCGGGUG UGGAGUUCUG GGGCUGCGUG GAACUUCGCU GGUAGUAGUC AAGCGAA    117

(2) INFORMATION FOR SEQ ID NO:95:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. AFRICANUM
        (B) STRAIN: CIP 140 030 001

(viii) POSITION IN GENOME:
        (B) MAP POSITION: 1409..1420, with respect to the numbering of
            E. coli (xi) SEQUENCE DESCRIPTION: SEQ ID NO:95:

GUAUGGCGUC CCUGAUGAAU CAGCGGUACU AACCACCCAA AACCGGAUCG ACCAUUCCUU    60

CGGGGCGUUG CCAUUCGGGG CUGCGUGGGA CCUUCGCUGG UAGUAGUCAA GCAAU    115

(2) INFORMATION FOR SEQ ID NO:96:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. MARINUM
        (B) STRAIN: CIP 140 120 001

(viii) POSITION IN GENOME:
        (B) MAP POSITION: 1409..1420, with respect to the numbering of
            E. coli (xi) SEQUENCE DESCRIPTION: SEQ ID NO:96:

GUGUGCGCGC CCGUGAUGAA UGAGCGGUAC UAACCACCCA AAACCGGAUC GAUCCAUAUC    60

CCUUCGGGGG CGUGGAGUUC CGGGCUGCG UGGAACCUUC GUUGGUAGUA GUCAAGCCAC    120

(2) INFORMATION FOR SEQ ID NO:97:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: rRNA ( v i ) ORIGINAL SOURCE:
     ( A ) ORGANISM: M. VACCAE ( v i i i ) POSITION IN GENOME:
     ( B ) MAP POSITION: 1409..1420, with respect to the numbering of
           E. coli ( x i ) SEQUENCE DESCRIPTION: SEQ ID NO:97:

| | | | | | | |
|---|---|---|---|---|---|---|
| GUGUGAGCGU | CCCUGAUGAA | UCAGCGGUAC | UAACCGCCCC | AAACCACAGU | CACCGAUCCU | 60 |
| UCAGGGUGAG | GGAUUGUGGG | CUGCGCGGGA | CCUUCGUUGG | UAGUAGUCAA | GCGAU | 115 |

( 2 ) INFORMATION FOR SEQ ID NO:98:

( i ) SEQUENCE CHARACTERISTICS:
          ( A ) LENGTH: 117 base pairs
          ( B ) TYPE: nucleic acid
          ( C ) STRANDEDNESS: single
          ( D ) TOPOLOGY: linear ( i i ) MOLECULE TYPE: rRNA ( v i ) ORIGINAL SOURCE:
          ( A ) ORGANISM: M. INTRACELLULARE
          ( B ) STRAIN: CIP 140 310 001

( v i i i ) POSITION IN GENOME:
          ( B ) MAP POSITION: 1409..1420, with respect to the numbering of
               E. coli ( x i ) SEQUENCE DESCRIPTION: SEQ ID NO:98:

| | | | | | | |
|---|---|---|---|---|---|---|
| GUAUGGGCGU | CCCUGAUGAA | UCAGCGGUAC | UAACCACCCA | AAACCGGAUC | GACCAUUCCU | 60 |
| UCGGGGGCAU | GGAGUUUCGG | GGCUGCGUGG | GACCUUCGCU | GGUAGUAGUC | AAGCAAU | 117 |

( 2 ) INFORMATION FOR SEQ ID NO:99:

( i ) SEQUENCE CHARACTERISTICS:
          ( A ) LENGTH: 115 base pairs
          ( B ) TYPE: nucleic acid
          ( C ) STRANDEDNESS: single
          ( D ) TOPOLOGY: linear ( i i ) MOLECULE TYPE: rRNA ( v i ) ORIGINAL SOURCE:
          ( A ) ORGANISM: M. SCROFULACEUM
          ( B ) STRAIN: CIP 140 220 001

( v i i i ) POSITION IN GENOME:
          ( B ) MAP POSITION: 1409..1420, with respect to the numbering of
               E. coli ( x i ) SEQUENCE DESCRIPTION: SEQ ID NO:99:

| | | | | | | |
|---|---|---|---|---|---|---|
| GUGUGGCGUC | CCUGAUGAAU | CAGCGGUACU | AACCACCCAA | AACCGGAUCG | ACCAUUCCUU | 60 |
| CGGGGCGUGG | AGUUUCGGGG | CUGCGUGGAA | CCUUCGCUGG | UAGUAGUCAA | GCAAU | 115 |

( 2 ) INFORMATION FOR SEQ ID NO:100:

( i ) SEQUENCE CHARACTERISTICS:
          ( A ) LENGTH: 114 base pairs
          ( B ) TYPE: nucleic acid
          ( C ) STRANDEDNESS: single
          ( D ) TOPOLOGY: linear ( i i ) MOLECULE TYPE: rRNA ( v i ) ORIGINAL SOURCE:
          ( A ) ORGANISM: M. SZULGAI
          ( B ) STRAIN: A 253

( v i i i ) POSITION IN GENOME:
          ( B ) MAP POSITION: 1409..1420, with respect to the numbering of E. coli (x i) SEQUENCE DESCRIPTION: SEQ ID NO:100:

```
GUGUGAGCGU  CCCUGAUGAA  UCAGCGGUAC  UAACCGCCCA  AAACCACGGU  CACCGAUCUU      60
CGGGGUNAGG  CCUCGUGGGC  UGCGUGGGAC  CUUCGUUCGU  UGUAGUCAAG  CGAU           114
```

(2) INFORMATION FOR SEQ ID NO:101:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. TERRAE
        (B) STRAIN: A 255

(viii) POSITION IN GENOME:
        (B) MAP POSITION: 1409..1420, with respect to the numbering of
            E. coli (x i) SEQUENCE DESCRIPTION: SEQ ID NO:101:

```
GUGUGAGCGU  CCCUGAUGAA  UCACGGUACU  AACCGCCCAA  AACCACGGUC  ACCGAUCCUU      60
CGGGGUGAGG  CAUUGUGGGG  CUGCGCGGGA  CCUUCGUUGG  UAGUAGUCAA  GCGAU          115
```

(2) INFORMATION FOR SEQ ID NO:102:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. CHELONAE
        (B) STRAIN: A 232

(viii) POSITION IN GENOME:
        (B) MAP POSITION: 1409..1420, with respect to the numbering of
            E. coli (x i) SEQUENCE DESCRIPTION: SEQ ID NO:102:

```
GUAUGUGCGU  CCAUGAUGAA  UCAGCGGUAC  UAACCAUCCA  AAACCACCGU  GAUCACACCU      60
UUCGGGGUGU  GGCGUUGGUG  GGGCUGCAUG  GGACCUUCGU  UGGUAGUAGU  CAAGCGAU      118
```

(2) INFORMATION FOR SEQ ID NO:103:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. FORTUITUM
        (B) STRAIN: CIP 140 410 001

(viii) POSITION IN GENOME:
        (B) MAP POSITION: 1409..1420, with respect to the numbering of
            E. coli (x i) SEQUENCE DESCRIPTION: SEQ ID NO:103:

```
GUAUGUGCGU  CCCUGAUGAA  UCCAUUGUGC  UAACCAUCCA  AAACCGUCGU  GACUGAUCUU      60
```

```
CGGGGUGAGG  CGUUGACGGG  GCUGCGUGGG  ACCCCGGUGG  GUAGUAGUCA  AGCGAU                116
```

( 2 ) INFORMATION FOR SEQ ID NO:104:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. PHLEI
        ( B ) STRAIN: A 247

( v i i i ) POSITION IN GENOME:
        ( B ) MAP POSITION: 1419..1420, with respect to the numbering of
        E. coli ( x i ) SEQUENCE DESCRIPTION: SEQ ID NO:104:

```
CCACCCAAAA  CCUGGCCGAU  CAUCUUCGGG  GUGACGGUUG  GGGGCUGNGU  GGGACNNGGG            60

UGGGUAGUAG  UCAAGCGAU                                                              79
```

( 2 ) INFORMATION FOR SEQ ID NO:105:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. CHITAE
        ( B ) STRAIN: ATCC 19627

( v i i i ) POSITION IN GENOME:
        ( B ) MAP POSITION: 1409..1420, with respect to the numbering of
        E. coli ( x i ) SEQUENCE DESCRIPTION: SEQ ID NO:105:

```
GUNUGAGCGU  CCCUGAUGAA  UCACCGGUAC  UAACCGCCCA  AAAGGUGAGC  AGAUCUAGAA            60

UCUUCGGGAA  AGGACUGUUG  CCGCUGCGCG  GGACUUCGGU  GGUAGUAGUC  AAGCGAU               117
```

( 2 ) INFORMATION FOR SEQ ID NO:106:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SMEGMATIS
        ( B ) STRAIN: A 251

( v i i i ) POSITION IN GENOME:
        ( B ) MAP POSITION: 1409..1420, with respect to the numbering of
        E. coli ( x i ) SEQUENCE DESCRIPTION: SEQ ID NO:106:

```
GUAUGUGCGU  CCAUGAUGAA  UCAGCGGUAC  UAACCAUCCA  AAACCACCGU  GACCGCACCU            60

UUCGGGGUGU  GGCGUUGGUG  GGGCUGCAUG  GGACCUUCGU  UGGUAGUAGU  CAAGCGAU              118
```

( 2 ) INFORMATION FOR SEQ ID NO:107:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. TUBERCULOSIS
  ( B ) STRAIN: A 203

( v i i i ) POSITION IN GENOME:
  ( B ) MAP POSITION: 1493..1515, with respect to the numbering of E. coli ( x i ) SEQUENCE DESCRIPTION: SEQ ID NO:107:

CAAAUCCGUG CGCGUCUACU AAUCCUGA 28

( 2 ) INFORMATION FOR SEQ ID NO:108:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. BOVIS BCG
  ( B ) STRAIN: H_P. PASTEUR ( v i i i ) POSITION IN GENOME:
  ( B ) MAP POSITION: 1493..1515, with respect to the numbering of E. coli ( x i ) SEQUENCE DESCRIPTION: SEQ ID NO:108:

CAAAUCCGGG CACUAACUCU UA 22

( 2 ) INFORMATION FOR SEQ ID NO:109:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. AFRICANUM
  ( B ) STRAIN: CIP 140 030 001

( v i i i ) POSITION IN GENOME:
  ( B ) MAP POSITION: 1493..1515, with respect to the numbering of E. coli ( x i ) SEQUENCE DESCRIPTION: SEQ ID NO:109:

CAAAUCCGUC GCUCACUAAU CCUGA 25

( 2 ) INFORMATION FOR SEQ ID NO:110:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: M. MARINUM ( B ) STRAIN: CIP 140 120 001

( v i i i ) POSITION IN GENOME:
                ( B ) MAP POSITION: 1493..1515, with respect to the numbering of
                      E. coli ( x i ) SEQUENCE DESCRIPTION: SEQ ID NO:110:

CAAAUCCGUC GUCAUUAAUC CUGA       24

( 2 ) INFORMATION FOR SEQ ID NO:111:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. VACCAE ( v i i i ) POSITION IN GENOME:
                ( B ) MAP POSITION: 1493..1515, with respect to the numbering of
                      E. coli ( x i ) SEQUENCE DESCRIPTION: SEQ ID NO:111:

NAAAUCCGGA UGUCACAUAU CCUGA       25

( 2 ) INFORMATION FOR SEQ ID NO:112:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. INTRACELLULARE
            ( B ) STRAIN: CIP 140 310 001

( v i i i ) POSITION IN GENOME:
                ( B ) MAP POSITION: 1493..1515, with respect to the numbering of
                      E. coli ( x i ) SEQUENCE DESCRIPTION: SEQ ID NO:112:

CAAAUCCGUC GCUCAUUAAU CCUGA       25

( 2 ) INFORMATION FOR SEQ ID NO:113:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. SCROFULACEUM
            ( B ) STRAIN: CIP 140 220 001

( v i i i ) POSITION IN GENOME:
                ( B ) MAP POSITION: 1493..1515, with respect to the numbering of
                      E. coli ( x i ) SEQUENCE DESCRIPTION: SEQ ID NO:113:

CAAAUCCGUC GCUCACCAAU CCUGA       25

( 2 ) INFORMATION FOR SEQ ID NO:114:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. SZULGAI
    ( B ) STRAIN: A 253

( v i i i ) POSITION IN GENOME:
    ( B ) MAP POSITION: 1493..1515, with respect to the numbering of E. coli ( x i ) SEQUENCE DESCRIPTION: SEQ ID NO:114:

CACAUCCGGA UGGNNCACAU CCUGA  25

( 2 ) INFORMATION FOR SEQ ID NO:115:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. TERRAE
    ( B ) STRAIN: A 255

( v i i i ) POSITION IN GENOME:
    ( B ) MAP POSITION: 1493..1515, with respect to the numbering of E. coli ( x i ) SEQUENCE DESCRIPTION: SEQ ID NO:115:

CAAAUCCGGA UGUCACAUAU CCUGA  25

( 2 ) INFORMATION FOR SEQ ID NO:116:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. CHELONAE
    ( B ) STRAIN: A 232

( v i i i ) POSITION IN GENOME:
    ( B ) MAP POSITION: 1493..1515, with respect to the numbering of E. coli ( x i ) SEQUENCE DESCRIPTION: SEQ ID NO:116:

UAAAUCCGUC UGGCGUAUAU CCUGA  25

( 2 ) INFORMATION FOR SEQ ID NO:117:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. FORTUITUM (B) STRAIN: CIP 140 410 001

(viii) POSITION IN GENOME:
                (B) MAP POSITION: 1493..1515, with respect to the numbering of
                    E. coli (xi) SEQUENCE DESCRIPTION: SEQ ID NO:117:

CAAAUCCGCG UUUCACAUAU CCUGA     25

(2) INFORMATION FOR SEQ ID NO:118:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. PHLEI
                (B) STRAIN: A 247

(viii) POSITION IN GENOME:
                (B) MAP POSITION: 1493..1515, with respect to the numbering of
                    E. coli (xi) SEQUENCE DESCRIPTION: SEQ ID NO:118:

CAAAUCCGUC AACAAUGAUG CCUGA     25

(2) INFORMATION FOR SEQ ID NO:119:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. CHITAE
                (B) STRAIN: ATCC 19627

(viii) POSITION IN GENOME:
                (B) MAP POSITION: 1493..1515, with respect to the numbering of
                    E. coli (xi) SEQUENCE DESCRIPTION: SEQ ID NO:119:

CAAAUCCGUC ACUCAUAUGU CUGA     24

(2) INFORMATION FOR SEQ ID NO:120:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. SMEGMATIS
                (B) STRAIN: A 251

(viii) POSITION IN GENOME:
                (B) MAP POSITION: 1493..1515, with respect to the numbering of
                    E. coli (xi) SEQUENCE DESCRIPTION: SEQ ID NO:120:

UAAAUCCGUC UGGCAUAUAU CCUGA     25

(2) INFORMATION FOR SEQ ID NO:121:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. TUBERCULOSIS
        (B) STRAIN: A 203

(viii) POSITION IN GENOME:
        (B) MAP POSITION: 1703..1761, with respect to the numbering of
            E. coli (xi) SEQUENCE DESCRIPTION: SEQ ID NO:121:

GGGGACCGGA AUAUCGUGAA CACCCUUGCG GUGGGAGCGG GAUCCGGUCG CAGAAACC     58

(2) INFORMATION FOR SEQ ID NO:122:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. BOVIS BCG
        (B) STRAIN: H_P. PASTEUR (viii) POSITION IN GENOME:
        (B) MAP POSITION: 1703..1761, with respect to the numbering of
            E. coli (xi) SEQUENCE DESCRIPTION: SEQ ID NO:122:

GGGGACCGAC AUAUCGUGAA CACCCUUGCG GUGGGAGCGG GAUCCGGUCG CAGAAACC     58

(2) INFORMATION FOR SEQ ID NO:123:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. AFRICANUM
        (B) STRAIN: CIP 140 030 001

(viii) POSITION IN GENOME:
        (B) MAP POSITION: 1703..1761, with respect to the numbering of
            E. coli (xi) SEQUENCE DESCRIPTION: SEQ ID NO:123:

GGGGGCCGGA AUACCGUGAA CACCCUUGCG GUGGGAGCGG GAUUCGGCCG CAGAAACC     58

(2) INFORMATION FOR SEQ ID NO:124:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: rRNA (vi) ORIGINAL SOURCE:

(A) ORGANISM: M. MARINUM
                (B) STRAIN: CIP 140 120 001

(viii) POSITION IN GENOME:
                (B) MAP POSITION: 1703..1761, with respect to the numbering of
                    E. coli (xi) SEQUENCE DESCRIPTION: SEQ ID NO:124:

GGGGACCGGA AUACCGUGAA CACCCUUGCG GUGGGAGCGG GAUUCGGUCG CAGAAACC        58

(2) INFORMATION FOR SEQ ID NO:125:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. VACCAE (viii) POSITION IN GENOME:
                (B) MAP POSITION: 1703..1761, with respect to the numbering of
                    E. coli (xi) SEQUENCE DESCRIPTION: SEQ ID NO:125:

AAGUGUAUUU UACUCAUGGA GCUGAAAUCA GUCGAAGAAC C        41

(2) INFORMATION FOR SEQ ID NO:126:

(i) SEQUENCE CHARACTERISTICS:
                (A) LENGTH: 58 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. INTRACELLULARE
                (B) STRAIN: CIP 140 310 001

(viii) POSITION IN GENOME:
                (B) MAP POSITION: 1703..1761, with respect to the numbering of
                    E. coli (xi) SEQUENCE DESCRIPTION: SEQ ID NO:126:

GGGGACCGGA AUACCGUGAA CACCCUUGCG GUGGGAGCGG GAUCCGGCCG CAGAAACC        58

(2) INFORMATION FOR SEQ ID NO:127:

(i) SEQUENCE CHARACTERISTICS:
                (A) LENGTH: 57 base pairs
                (B) TYPE: nucleic acid
                (C) STRANDEDNESS: single
                (D) TOPOLOGY: linear (ii) MOLECULE TYPE: rRNA (vi) ORIGINAL SOURCE:
                (A) ORGANISM: M. SCROFULACEUM
                (B) STRAIN: CIP 140 220 001

(viii) POSITION IN GENOME:
                (B) MAP POSITION: 1703..1761, with respect to the numbering of
                    E. coli (xi) SEQUENCE DESCRIPTION: SEQ ID NO:127:

GGGGGCCGAA AUACCGUGAA CACCUUGCGG UGGGAGCGGG AUUCGGCCGC AGAAACC        57

( 2 ) INFORMATION FOR SEQ ID NO:128:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SZULGAI
        ( B ) STRAIN: A 253

( v i i i ) POSITION IN GENOME:
        ( B ) MAP POSITION: 1703..1761, with respect to the numbering of
            E. coli ( x i ) SEQUENCE DESCRIPTION: SEQ ID NO:128:

GGGGACCUCC AUACCGUCAA CCGGUUUACC CUGGGCAGCG GGAGGGGUGG CACAAACC    58

( 2 ) INFORMATION FOR SEQ ID NO:129:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. KANSASII
        ( B ) STRAIN: CIP 140 110 001

( v i i i ) POSITION IN GENOME:
        ( B ) MAP POSITION: 1703..1761, with respect to the numbering of
            E. coli ( x i ) SEQUENCE DESCRIPTION: SEQ ID NO:129:

AAUUCGGUCG CACAAACC    18

( 2 ) INFORMATION FOR SEQ ID NO:130:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. TERRAE
        ( B ) STRAIN: A 255

( v i i i ) POSITION IN GENOME:
        ( B ) MAP POSITION: 1703..1761, with respect to the numbering of
            E. coli ( x i ) SEQUENCE DESCRIPTION: SEQ ID NO:130:

GGGGACCUCC AUACCGUCAA CCGGUUUACU CGGGGCAGCG GGAGGGGUG GCACAAACC    59

( 2 ) INFORMATION FOR SEQ ID NO:131:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:

```
            ( A ) ORGANISM: M. CHELONAE
            ( B ) STRAIN: A 232

( v i i i ) POSITION IN GENOME:
            ( B ) MAP POSITION: 1703..1761, with respect to the numbering of
                E. coli ( x i ) SEQUENCE DESCRIPTION: SEQ ID NO:131:
```

GGGGACCCAC AUGGCGUGUA AGCCUUUACG GCCCAAGCGU GAGUGGGUGG CACAAACC    58

( 2 ) INFORMATION FOR SEQ ID NO:132:

```
    ( i ) SEQUENCE CHARACTERISTICS:
            ( A ) LENGTH: 59 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. FLAVESCENS
            ( B ) STRAIN: CIP 140 230 001

( v i i i ) POSITION IN GENOME:
            ( B ) MAP POSITION: 1703..1761, with respect to the numbering of
                E. coli ( x i ) SEQUENCE DESCRIPTION: SEQ ID NO:132:
```

GGGGACCCCC ACACCGUCAA GGCCCUUGCG GCCGGCAGCG GGAGGGGGUG GCACAAACC    59

( 2 ) INFORMATION FOR SEQ ID NO:133:

```
    ( i ) SEQUENCE CHARACTERISTICS:
            ( A ) LENGTH: 59 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. FORTUITUM
            ( B ) STRAIN: CIP 140 410 001

( v i i i ) POSITION IN GENOME:
            ( B ) MAP POSITION: 1703..1761, with respect to the numbering of
                E. coli ( x i ) SEQUENCE DESCRIPTION: SEQ ID NO:133:
```

GGGGACCCCC ACACCGUCAA GGCUCUUGCG GCCGGCAGCG GGAGGGGGUG GCACAAACC    59

( 2 ) INFORMATION FOR SEQ ID NO:134:

```
    ( i ) SEQUENCE CHARACTERISTICS:
            ( A ) LENGTH: 59 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: M. PHLEI
            ( B ) STRAIN: A 247

( v i i i ) POSITION IN GENOME:
            ( B ) MAP POSITION: 1703..1761, with respect to the numbering of
                E. coli ( x i ) SEQUENCE DESCRIPTION: SEQ ID NO:134:
```

GGGGACCCCA CUACCGUCAU GGCUCUUGCG GCCGGCAGCG GGGUGGGUG GCACAAACC    59

( 2 ) INFORMATION FOR SEQ ID NO:135:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. CHITAE
        ( B ) STRAIN: ATCC 19627

( v i i i ) POSITION IN GENOME:
        ( B ) MAP POSITION: 1703..1761, with respect to the numbering of
        E. coli ( x i ) SEQUENCE DESCRIPTION: SEQ ID NO:135:

```
GGGGACCCAC  AUGGCGUGAU  CCAUCUUCGC  GGUGGUGAGC  CUGAGUCGGU  UGCUCGAACC          60
```

( 2 ) INFORMATION FOR SEQ ID NO:136:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SMEGMATIS
        ( B ) STRAIN: A 251

( v i i i ) POSITION IN GENOME:
        ( B ) MAP POSITION: 1703..1761, with respect to the numbering of
        E. coli ( x i ) SEQUENCE DESCRIPTION: SEQ ID NO:136:

```
GGGGACCCAC  AUGGCGUGUA  AGCCUUUACG  GCCCAAGCGU  GAGUGGGUGG  CACAAACC            58
```

( 2 ) INFORMATION FOR SEQ ID NO:137:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. TUBERCULOSIS
        ( B ) STRAIN: A 203

( v i i i ) POSITION IN GENOME:
        ( B ) MAP POSITION: 1854..1876, with respect to the numbering of
        E. coli ( x i ) SEQUENCE DESCRIPTION: SEQ ID NO:137:

```
AGAGGACCCG  UUAACCCGCA  AGGGUGA                                                 27
```

( 2 ) INFORMATION FOR SEQ ID NO:138:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
                        ( A ) ORGANISM: M. BOVIS BCG
                        ( B ) STRAIN: H_P. PASTEUR ( v i i i ) POSITION IN GENOME:
                        ( B ) MAP POSITION: 1854..1876, with respect to the numbering of
                              E. coli ( x i ) SEQUENCE DESCRIPTION: SEQ ID NO:138:

AGAGGACCCG UUAACCCGCA AGGGUGA                                                            27

( 2 ) INFORMATION FOR SEQ ID NO:139:

( i ) SEQUENCE CHARACTERISTICS:
                        ( A ) LENGTH: 27 base pairs
                        ( B ) TYPE: nucleic acid
                        ( C ) STRANDEDNESS: single
                        ( D ) TOPOLOGY: linear ( i i ) MOLECULE TYPE: rRNA ( v i ) ORIGINAL SOURCE:
                        ( A ) ORGANISM: M. AFRICANUM
                        ( B ) STRAIN: CIP 140 030 001

( v i i i ) POSITION IN GENOME:
                        ( B ) MAP POSITION: 1854..1876, with respect to the numbering of
                              E. coli ( x i ) SEQUENCE DESCRIPTION: SEQ ID NO:139:

AGAGGACCCG UUAACCCGUA AGGGUGA                                                            27

( 2 ) INFORMATION FOR SEQ ID NO:140:

( i ) SEQUENCE CHARACTERISTICS:
                        ( A ) LENGTH: 27 base pairs
                        ( B ) TYPE: nucleic acid
                        ( C ) STRANDEDNESS: single
                        ( D ) TOPOLOGY: linear ( i i ) MOLECULE TYPE: rRNA ( v i ) ORIGINAL SOURCE:
                        ( A ) ORGANISM: M. MARINUM
                        ( B ) STRAIN: CIP 140 120 001

( v i i i ) POSITION IN GENOME:
                        ( B ) MAP POSITION: 1854..1876, with respect to the numbering of
                              E. coli ( x i ) SEQUENCE DESCRIPTION: SEQ ID NO:140:

AGAGGACCCG UUAACUCGUA AGGGUGA                                                            27

( 2 ) INFORMATION FOR SEQ ID NO:141:

( i ) SEQUENCE CHARACTERISTICS:
                        ( A ) LENGTH: 26 base pairs
                        ( B ) TYPE: nucleic acid
                        ( C ) STRANDEDNESS: single
                        ( D ) TOPOLOGY: linear ( i i ) MOLECULE TYPE: rRNA ( v i ) ORIGINAL SOURCE:
                        ( A ) ORGANISM: M. VACCAE ( v i i i ) POSITION IN GENOME:
                        ( B ) MAP POSITION: 1854..1876, with respect to the numbering of
                              E. coli ( x i ) SEQUENCE DESCRIPTION: SEQ ID NO:141:

AGAGGACCGG UUAGCCUUCG GGGUGA                                                             26

( 2 ) INFORMATION FOR SEQ ID NO:142:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. INTRACELLULARE
        ( B ) STRAIN: CIP 140 310 001

( v i i i ) POSITION IN GENOME:
        ( B ) MAP POSITION: 1854..1876, with respect to the numbering of E. coli ( x i ) SEQUENCE DESCRIPTION: SEQ ID NO:142:

AGAGGACCCG UUAACCGUAA GGUGA     25

( 2 ) INFORMATION FOR SEQ ID NO:143:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SCROFULACEUM
        ( B ) STRAIN: CIP 140 220 001

( v i i i ) POSITION IN GENOME:
        ( B ) MAP POSITION: 1854..1876, with respect to the numbering of E. coli ( x i ) SEQUENCE DESCRIPTION: SEQ ID NO:143:

AGAGGACCCG UUAACCGUAA GGUGA     25

( 2 ) INFORMATION FOR SEQ ID NO:144:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SZULGAI
        ( B ) STRAIN: A 253

( v i i i ) POSITION IN GENOME:
        ( B ) MAP POSITION: 1854..1876, with respect to the numbering of E. coli ( x i ) SEQUENCE DESCRIPTION: SEQ ID NO:144:

AGAGGACCGG UUAACCUUCG GGUGA     26

( 2 ) INFORMATION FOR SEQ ID NO:145:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: rRNA (vi) ORIGINAL SOURCE:
    (A) ORGANISM: M. KANSASII
    (B) STRAIN: CIP 140 110 001

(viii) POSITION IN GENOME:
    (B) MAP POSITION: 1854..1876, with respect to the numbering of
        E. coli (xi) SEQUENCE DESCRIPTION: SEQ ID NO:145:

AGAGGACCCG UUAACCCGCA AGGGUGA　　　　27

(2) INFORMATION FOR SEQ ID NO:146:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. TERRAE
        (B) STRAIN: A 255

(viii) POSITION IN GENOME:
        (B) MAP POSITION: 1854..1876, with respect to the numbering of
            E. coli (xi) SEQUENCE DESCRIPTION: SEQ ID NO:146:

AGAGGACCGG UUAACUUCGG GGUGA　　　　25

(2) INFORMATION FOR SEQ ID NO:147:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. CHELONAE
        (B) STRAIN: A 232

(viii) POSITION IN GENOME:
        (B) MAP POSITION: 1854..1876, with respect to the numbering of
            E. coli (xi) SEQUENCE DESCRIPTION: SEQ ID NO:147:

AGAGGACCCG UUAAGUCCCU UUGGGGGUGA　　　　30

(2) INFORMATION FOR SEQ ID NO:148:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: M. FLAVESCENS
        (B) STRAIN: CIP 140 230 001

(viii) POSITION IN GENOME:
        (B) MAP POSITION: 1854..1876, with respect to the numbering of
            E. coli (xi) SEQUENCE DESCRIPTION: SEQ ID NO:148:

AGAGGACCCG UUAACCCGCA AGGGUGA　　　　27

( 2 ) INFORMATION FOR SEQ ID NO:149:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: M. FORTUITUM
( B ) STRAIN: CIP 140 410 001

( v i i i ) POSITION IN GENOME:
( B ) MAP POSITION: 1854..1876, with respect to the numbering of E. coli ( x i ) SEQUENCE DESCRIPTION: SEQ ID NO:149:

AGAGGACCUG UUAACCUUCG GGGUGA    26

( 2 ) INFORMATION FOR SEQ ID NO:150:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: M. PHLEI
( B ) STRAIN: A 247

( v i i i ) POSITION IN GENOME:
( B ) MAP POSITION: 1854..1876, with respect to the numbering of E. coli ( x i ) SEQUENCE DESCRIPTION: SEQ ID NO:150:

AGAGGACCCG UUAACCCUUU GCGGGGGUGA    30

( 2 ) INFORMATION FOR SEQ ID NO:151:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: M. CHITAE
( B ) STRAIN: ATCC 19627

( v i i i ) POSITION IN GENOME:
( B ) MAP POSITION: 1854..1876, with respect to the numbering of E. coli ( x i ) SEQUENCE DESCRIPTION: SEQ ID NO:151:

AGAGGACCUG UUAACCUUUC GGGGGUGA    28

( 2 ) INFORMATION FOR SEQ ID NO:152:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
   ( A ) ORGANISM: M. SMEGMATIS
   ( B ) STRAIN: A 251

( v i i i ) POSITION IN GENOME:
   ( B ) MAP POSITION: 1854..1876, with respect to the numbering of
       E. coli ( x i ) SEQUENCE DESCRIPTION: SEQ ID NO:152:

AGAGGACCCG UUAACUCCCU UUGGGGGUGA                                30

( 2 ) INFORMATION FOR SEQ ID NO:153:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. TUBERCULOSIS
      ( B ) STRAIN: A 203

( v i i i ) POSITION IN GENOME:
      ( B ) MAP POSITION: 2126..2161, with respect to the numbering of
          E. coli ( x i ) SEQUENCE DESCRIPTION: SEQ ID NO:153:

AGACUGUGAA ACCUCGACGC CAGUUGGGGC GGAGUC                          36

( 2 ) INFORMATION FOR SEQ ID NO:154:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. AFRICANUM
      ( B ) STRAIN: CIP 140 030 001

( v i i i ) POSITION IN GENOME:
      ( B ) MAP POSITION: 2126..2161, with respect to the numbering of
          E. coli ( x i ) SEQUENCE DESCRIPTION: SEQ ID NO:154:

AGACUUUGAA GCACAGACGC CAGUUUGUGU GGAGUC                          36

( 2 ) INFORMATION FOR SEQ ID NO:155:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: rRNA ( v i ) ORIGINAL SOURCE:
      ( A ) ORGANISM: M. MARINUM
      ( B ) STRAIN: CIP 140 120 001

( v i i i ) POSITION IN GENOME:
      ( B ) MAP POSITION: 2126..2161, with respect to the numbering of
          E. coli ( x i ) SEQUENCE DESCRIPTION: SEQ ID NO:155:

```
AGACUGUGAA ACUCCAACGC CAGUUGGGGC GGAGUC                                                    36
```

( 2 ) INFORMATION FOR SEQ ID NO:156:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. INTRACELLULARE
    ( B ) STRAIN: CIP 140 310 001

( v i i i ) POSITION IN GENOME:
    ( B ) MAP POSITION: 2126..2161, with respect to the numbering of
      E. coli ( x i ) SEQUENCE DESCRIPTION: SEQ ID NO:156:

```
AGACUGUGAA AUACAGACGC CAGUUUGUAU GGAGUC                                                    36
```

( 2 ) INFORMATION FOR SEQ ID NO:157:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. SCROFULACEUM
    ( B ) STRAIN: CIP 140 220 001

( v i i i ) POSITION IN GENOME:
    ( B ) MAP POSITION: 2126..2161, with respect to the numbering of
      E. coli ( x i ) SEQUENCE DESCRIPTION: SEQ ID NO:157:

```
AGACUGUGAA ACCCUAACGC CAGUUGGGGC GGAGUC                                                    36
```

( 2 ) INFORMATION FOR SEQ ID NO:158:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
    ( A ) ORGANISM: M. SZULGAI
    ( B ) STRAIN: A 253

( v i i i ) POSITION IN GENOME:
    ( B ) MAP POSITION: 2126..2161, with respect to the numbering of
      E. coli ( x i ) SEQUENCE DESCRIPTION: SEQ ID NO:158:

```
AGACUGUGAA GCGGCCACGC CAGUGGUUGU GGAGUC                                                    36
```

( 2 ) INFORMATION FOR SEQ ID NO:159:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: rRNA ( v i ) ORIGINAL SOURCE:
               ( A ) ORGANISM: M. KANSASII
               ( B ) STRAIN: CIP 140 110 001

( v i i i ) POSITION IN GENOME:
               ( B ) MAP POSITION: 2126..2161, with respect to the numbering of
                     E. coli ( x i ) SEQUENCE DESCRIPTION: SEQ ID NO:159:

UGACUGUGAA CCUCUAACGC CAGUUGGGUG GAGUC                                          35

( 2 ) INFORMATION FOR SEQ ID NO:160:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( i i ) MOLECULE TYPE: rRNA ( v i ) ORIGINAL SOURCE:
               ( A ) ORGANISM: M. TERRAE
               ( B ) STRAIN: A 255

( v i i i ) POSITION IN GENOME:
               ( B ) MAP POSITION: 2126..2161, with respect to the numbering of
                     E. coli ( x i ) SEQUENCE DESCRIPTION: SEQ ID NO:160:

AGACUGUGAA GCGGCCACGC CAGUGGUUGU GGAGUC                                         36

( 2 ) INFORMATION FOR SEQ ID NO:161:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( i i ) MOLECULE TYPE: rRNA ( v i ) ORIGINAL SOURCE:
               ( A ) ORGANISM: M. CHELONAE
               ( B ) STRAIN: A 232

( v i i i ) POSITION IN GENOME:
               ( B ) MAP POSITION: 2126..2161, with respect to the numbering of
                     E. coli ( x i ) SEQUENCE DESCRIPTION: SEQ ID NO:161:

AGACUGUGAA GCUCACACGC CAGUGUGGGU GGAGUC                                         36

( 2 ) INFORMATION FOR SEQ ID NO:162:

( i ) SEQUENCE CHARACTERISTICS:
               ( A ) LENGTH: 36 base pairs
               ( B ) TYPE: nucleic acid
               ( C ) STRANDEDNESS: single
               ( D ) TOPOLOGY: linear ( i i ) MOLECULE TYPE: rRNA ( v i ) ORIGINAL SOURCE:
               ( A ) ORGANISM: M. FORTUITUM
               ( B ) STRAIN: CIP 140 410 001

( v i i i ) POSITION IN GENOME:
               ( B ) MAP POSITION: 2126..2161, with respect to the numbering of
                     E. coli ( x i ) SEQUENCE DESCRIPTION: SEQ ID NO:162:

AGACUGUGAA GCAGCCACGC CAGUUGUUGU GGAGUC    36

( 2 ) INFORMATION FOR SEQ ID NO:163:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. PHLEI
        ( B ) STRAIN: A 247

( v i i i ) POSITION IN GENOME:
        ( B ) MAP POSITION: 2126..2161, with respect to the numbering of
            E. coli ( x i ) SEQUENCE DESCRIPTION: SEQ ID NO:163:

AGACUGUGAA GCUUCGACGC CAGUUCGGGU GGAGUC    36

( 2 ) INFORMATION FOR SEQ ID NO:164:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. CHITAE
        ( B ) STRAIN: ATCC 19627

( v i i i ) POSITION IN GENOME:
        ( B ) MAP POSITION: 2126..2161, with respect to the numbering of
            E. coli ( x i ) SEQUENCE DESCRIPTION: SEQ ID NO:164:

AGACUGUGAA GCAGUAACGC CAGUUAUUGU GGAGUC    36

( 2 ) INFORMATION FOR SEQ ID NO:165:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. SMEGMATIS
        ( B ) STRAIN: A 251

( v i i i ) POSITION IN GENOME:
        ( B ) MAP POSITION: 2126..2161, with respect to the numbering of
            E. coli ( x i ) SEQUENCE DESCRIPTION: SEQ ID NO:165:

AGACUGUGAA GCUCACACGC CAGUGUGGGU GGAGUC    36

( 2 ) INFORMATION FOR SEQ ID NO:166:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear (i i) MOLECULE TYPE: rRNA (v i) ORIGINAL SOURCE:
    (A) ORGANISM: M. BOVIS
    (B) STRAIN: ATCC 19210

(v i i i) POSITION IN GENOME:
    (B) MAP POSITION: 1409..1420, with respect to the numbering of
    E. coli (x i) SEQUENCE DESCRIPTION: SEQ ID NO:166:

```
GGCGACCGUG ACGAAUCAGC GGUACUAACC ACCCAAAACC GGAUCGAUCA CUCCCCUUCG      60
GGGGUGUGGA GUUCUGGGGC UGCGUGGG                                         88
```

(2) INFORMATION FOR SEQ ID NO:167:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: M. AVIUM
        (B) STRAIN: DSM 43216

(v i i i) POSITION IN GENOME:
        (B) MAP POSITION: 1409..1420, with respect to the numbering of
        E. coli (x i) SEQUENCE DESCRIPTION: SEQ ID NO:167:

```
GUAUAGGCGU CCCUGAUGAA UCAGCGGUAC UAACCACCCA AAACCGGAUC GACCAUUCCC      60
CUUCGGGGC AUGGAGUUUC GGGGCUGCGU GGGACCUUCG CUGGUAGUAG UCAAGCGAU       119
```

(2) INFORMATION FOR SEQ ID NO:168:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: M. INTRACELLULARE
        (B) STRAIN: ATCC 35764

(v i i i) POSITION IN GENOME:
        (B) MAP POSITION: 1409..1420, with respect to the numbering of
        E. coli (x i) SEQUENCE DESCRIPTION: SEQ ID NO:168:

```
GUAUGGGCGU CCCUGAUGAA UCAGCGGUAC UAACCACCCA AAACCGGAUC GACCAUUCCC      60
CUUCGGGGC AUGGAGUUUC GGGGCUGCGU GGGACCUUCG CUGGUAGUAG GUCAAGCGAU      120
```

(2) INFORMATION FOR SEQ ID NO:169:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (i i) MOLECULE TYPE: rRNA (v i) ORIGINAL SOURCE:
        (A) ORGANISM: M. INTRACELLULARE -continued (B) STRAIN: ATCC 35767

(viii) POSITION IN GENOME:
          (B) MAP POSITION: 1409..1420, with respect to the numbering of
              E. coli (xi) SEQUENCE DESCRIPTION: SEQ ID NO:169:

GUAUGGGCGU  CCCUGAUGAA  UCAGCGGUAC  UAACCACCCA  AAACCGGAUC  GACCAUUCCC      60

CUUCGGGGC  AUGGCGAUUC  GGGGCUGCGU  GGGACCUUCG  CUGGUAGUAG  GUCAAGCAAU     120

(2) INFORMATION FOR SEQ ID NO:170:

(i) SEQUENCE CHARACTERISTICS:
          (A) LENGTH: 118 base pairs
          (B) TYPE: nucleic acid
          (C) STRANDEDNESS: single
          (D) TOPOLOGY: linear (ii) MOLECULE TYPE: rRNA (vi) ORIGINAL SOURCE:
          (A) ORGANISM: M. INTRACELLULARE
          (B) STRAIN: ATCC 35847

(viii) POSITION IN GENOME:
          (B) MAP POSITION: 1409..1420, with respect to the numbering of
              E. coli (xi) SEQUENCE DESCRIPTION: SEQ ID NO:170:

GUAUAGGCGU  CCCUGAUGAA  UCAGUGGUAC  UAACCACCCA  AAUGGUGGUC  UAUCAAUNCC     60

CUUCNGGGUG  CGAGGAUCAC  CGGCUGCGUG  GGACCUUCGC  UGGUAGUAGU  CAAGCGAU      118

(2) INFORMATION FOR SEQ ID NO:171:

(i) SEQUENCE CHARACTERISTICS:
          (A) LENGTH: 87 base pairs
          (B) TYPE: nucleic acid
          (C) STRANDEDNESS: single
          (D) TOPOLOGY: linear (ii) MOLECULE TYPE: rRNA (vi) ORIGINAL SOURCE:
          (A) ORGANISM: M. GASTRI
          (B) STRAIN: C 097biomerieux (viii) POSITION IN GENOME:
          (B) MAP POSITION: 1409..1420, with respect to the numbering of
              E. coli (xi) SEQUENCE DESCRIPTION: SEQ ID NO:171:

CCGUGAUGAA  UCAGCGGUAC  UAACCACCAA  AACCGGAUCG  AUCACUCCCC  UUCGGGGCG      60

UGGCGGUCUG  GCGCUGCGUG  GAGCCUU                                            87

(2) INFORMATION FOR SEQ ID NO:172:

(i) SEQUENCE CHARACTERISTICS:
          (A) LENGTH: 98 base pairs
          (B) TYPE: nucleic acid
          (C) STRANDEDNESS: single
          (D) TOPOLOGY: linear (ii) MOLECULE TYPE: rRNA (vi) ORIGINAL SOURCE:
          (A) ORGANISM: M. SIMIAE
          (B) STRAIN: ATCC 25275

(viii) POSITION IN GENOME:
          (B) MAP POSITION: 1409..1420, with respect to the numbering of
              E. coli ( x i ) SEQUENCE DESCRIPTION: SEQ ID NO:172:

UCCAUUCUGC UAACCACCCA AAUGGCGGUC UAUCAAUCCC UUCGGGGUGC GAAGCAUCGC       60

CGGCUGCGUG GGACCCGGGU GGGUAGUAGU CAAGCAAU       98

( 2 ) INFORMATION FOR SEQ ID NO:173:

( i ) SEQUENCE CHARACTERISTICS:
        ( A ) LENGTH: 109 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. XENOPI
        ( B ) STRAIN: C 112biomerieux ( v i i i ) POSITION IN GENOME:
        ( B ) MAP POSITION: 1409..1420, with respect to the numbering of
            E. coli ( x i ) SEQUENCE DESCRIPTION: SEQ ID NO:173:

CCAUACCGAA UCGGAUCUGC UAACCACCCA AACGGUGGGU GAUCACGCCC UUUCGGGGU       60

GUGGGGCCCG CCCGCUGCGU GGGGCCCGGU CCGCUAGUAG GUAAGCGAG       109

( 2 ) INFORMATION FOR SEQ ID NO:174:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. TERRAE
        ( B ) STRAIN: C 104biomerieux ( v i i i ) POSITION IN GENOME:
        ( B ) MAP POSITION: 1409..1420, with respect to the numbering of
            E. coli ( x i ) SEQUENCE DESCRIPTION: SEQ ID NO:174:

UGUCCGGCGA CCGUGAUGAA UCAGCGGUAC UAACCACCCA AAACCGGAUC GAUCACUCCC       60

CUUCGGGGGC GUGGAGGUCU GGGGCUGCGU GGAGCCUCCG CUGG       104

( 2 ) INFORMATION FOR SEQ ID NO:175:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. ASIATICUM
        ( B ) STRAIN: ATCC 25276

( v i i i ) POSITION IN GENOME:
        ( B ) MAP POSITION: 1409..1420, with respect to the numbering of
            E. coli ( x i ) SEQUENCE DESCRIPTION: SEQ ID NO:175:

CCCGUGAUGA AUCAUCUGUG CUAACCACCC AAAUGGUCGC UGAUCAAUCC CUUCGGGGUG       60

CGACGGUGAC CGGCUGCGUG GGA 83

( 2 ) INFORMATION FOR SEQ ID NO:176:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. GORDONAE
        ( B ) STRAIN: TMC 1324

( v i i i ) POSITION IN GENOME:
        ( B ) MAP POSITION: 1409..1420, with respect to the numbering of
            E. coli ( x i ) SEQUENCE DESCRIPTION: SEQ ID NO:176:

GUGCGCGCCC GUGAUGAAUC AAUUGUGCUA ACCACCCAAA UGGUACGCUG AUCAAUCCCU 60

UCGGGGUGCG ACGGUGACCG GCUGCGUGGG ACCCCGGUUG 100

( 2 ) INFORMATION FOR SEQ ID NO:177:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. KANSASII
        ( B ) STRAIN: TMC 1204

( v i i i ) POSITION IN GENOME:
        ( B ) MAP POSITION: 1409..1420, with respect to the numbering of
            E. coli ( x i ) SEQUENCE DESCRIPTION: SEQ ID NO:177:

UGGGCUUCGG AUGAAUCAGC GGUUCUAACC ACCCAAAACC GGAUCGAUCA CUCCCCUUCG 60

GGGGCGUGGA GGUCUGGGGC UGCGUGGAGG 90

( 2 ) INFORMATION FOR SEQ ID NO:178:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: M. BOVIS BCG
        ( B ) STRAIN: C 080biomerieux ( v i i i ) POSITION IN GENOME:
        ( B ) MAP POSITION: 1409..1420, with respect to the numbering of
            E. coli ( x i ) SEQUENCE DESCRIPTION: SEQ ID NO:178:

GGCGACCGUG ACGAAUCAGC GGUACUAACC ACCCAAAACC GGAUCGAUCA CUCCCCUUCG 60

GGGGUGUGGA GUUCUGGGGC UGCGUGGAA CUU 93

We claim:

1. A single-stranded nucleotide fragment of no more than one hundred modified or unmodified nucleotides, wherein said fragment comprises a nucleotide sequence selected from the group consisting of the following nucleotide sequences of a 23S ribosomal RNA of a species of the genus Mycobacterium:

beginning at nucleotide No. 137 and ending at nucleotide No. 179, beginning at nucleotide No. 206 and ending at nucleotide No. 248, beginning at nucleotide No. 269 and ending at nucleotide No. 289 of a 23S ribosomal RNA of species other than *M. tuberculosis* and *M. fortuitum*, beginning at nucleotide No. 289 and ending at nucleotide No. 290 of a 23S ribosomal RNA of species other than *M. tuberculosis* and *M. fortuitum*, beginning at nucleotide No. 341 and ending at nucleotide No. 372, beginning at nucleotide No. 645 and ending at nucleotide No. 661 of a 23S ribosomal RNA of species other than *M. tuberculosis* and *M. fortuitum*, beginning at nucleotide No. 1201 and ending at nucleotide No. 1242, beginning at nucleotide No. 1409 and ending at nucleotide No. 1420 of a 23S ribosomal RNA of species other than *M. tuberculosis, M. marinum, M. scrofulaceum, M. avium* TMC 724, *M. leprae, M. kansasii, M. asiaticum, M. ulcerans* ATCC 19423, *M. malmoense* ATCC 29571, *M. gordonae, M. lactae* ATCC 25854, *M. aurum* ATCC 23366, *M. vaccae* ATCC 15483 and *M. neoaurum* ATCC 25795, beginning at nucleotide No. 1493 and ending at nucleotide No. 1515, beginning at nucleotide No. 1703 and ending at nucleotide No. 1761, beginning at nucleotide No. 1854 and ending at nucleotide No. 1876 of a 23S ribosomal RNA of species other than *M. tuberculosis, M. kansasii* and *M. fortuitum*, beginning at nucleotide No. 2126 and ending at nucleotide No. 2161 of a 23S ribosomal RNA of species other than *M. avium, M. tuberculosis, M. kansasii* and *M. fortuitum*, their corresponding DNA sequences, and sequences fully complementary to said RNA and DNA sequences, the numbers of the nucleotides corresponding to their position relative to the nucleotide sequence of *Escherichia coli* 23S ribosomal RNA, wherein each said fragment selectively hybridizes to RNA or DNA of only one or two species of the genus Mycobacterium.

2. The fragment as claimed in claim 1, wherein said fragment comprises at least one sequence selected from the group consisting of: SEQ ID NO 1 to SEQ ID NO 28, SEQ ID NO 30 to SEQ ID NO 37, SEQ ID NO 39 to SEQ ID NO 41, SEQ ID NO 43 to SEQ ID NO 49, SEQ ID NO 51 to SEQ ID NO 67, SEQ ID NO 69 to SEQ ID NO 75, SEQ ID NO 77 to SEQ ID NO 93, SEQ ID NO 95, SEQ ID NO 97, SEQ ID NO 98, SEQ ID NO 100 to SEQ ID NO 136, SEQ ID NO 139 to SEQ ID NO 144, SEQ ID NO 146 to SEQ ID NO 147, SEQ ID NO 150 to SEQ ID NO 152, SEQ ID NO 154 to SEQ ID NO 158, SEQ ID NO 160, SEQ ID NO 161, SEQ ID NO 163 to SEQ ID NO 174 and SEQ ID NO 178, and their fully complementary sequences.

3. A single-stranded nucleotide fragment of DNA, which is a reverse transcription product of a RNA fragment as claimed in claim 1, or its fully complementary fragment.

4. A single-stranded nucleotide fragment of genomic DNA, whose transcription product is a RNA fragment as claimed in claim 1, or its fully complementary fragment.

5. A probe for the identification of one or two species of bacteria of the genus Mycobacterium, said probe comprising, as its sole nucleotide sequence, a probe sequence of no more than one hundred modified or unmodified nucleotides, said probe sequence comprising at least eight contiguous modified or unmodified nucleotides of the nucleotide sequence of the fragment as claimed in claim 1, or a homologous sequence of at least eight nucleotides that hybridizes to said nucleotide sequence of said fragment, wherein said probe selectively hybridizes to RNA or DNA of only one or two species of the genus Mycobacterium.

6. The probe as claimed in claim 5, which comprises a sequence of eight to fifty modified or unmodified nucleotides of the nucleotide sequence of said fragment.

7. A probe for the identification of one or two species of bacteria of the genus Mycobacterium, said probe comprising, as its sole nucleotide sequence, a first sequence of no more than one hundred modified or unmodified nucleotides, said first sequence comprising a second sequence selected from the group consisting of the following sequences:

beginning at nucleotide No. 10 and ending at nucleotide No. 24 of at least one of sequences SEQ ID NO 1 to 14, beginning at nucleotide No. 26 and ending at nucleotide No. 45 of at least one of sequences SEQ ID NO 1 to 14, beginning at nucleotide No. 1 and ending at nucleotide No. 20 of at least one of sequences SEQ ID NO 15 to 28, beginning at nucleotide No. 26 and ending at nucleotide No. 43 of at least one of sequences SEQ ID NO 15 to 28, beginning at nucleotide No. 4 and ending at nucleotide No. 22 of at least one of sequences SEQ ID NO 29 to 41, beginning at nucleotide No. 12 and ending at nucleotide No. 29 of at least one of sequences SEQ ID NO 42 to 53, beginning at nucleotide No. 36 and ending at nucleotide No. 56 of at least one of sequences SEQ ID NO 42 to 53, beginning at nucleotide No. 13 and ending at nucleotide No. 32 of at least one of sequences SEQ ID NO 54 to 67, beginning at nucleotide No. 5 and ending at nucleotide No. 23 of at least one of sequences SEQ ID NO 68 to 79, beginning at nucleotide No. 15 and ending at nucleotide No. 33 of at least one of sequences SEQ ID NO 80 to 93, beginning at nucleotide No. 1 and ending at nucleotide No. 21 of at least one of sequences SEQ ID NO 94 to 106 and SEQ ID NO 166 to 178, beginning at nucleotide No. 44 and ending at nucleotide No. 76 of at least one of sequences SEQ ID NO 94 to 106 and SEQ ID NO 166 to 178, beginning at nucleotide No. 67 and ending at nucleotide No. 85 of at least one of sequences SEQ ID NO 94 to 106 and SEQ ID NO 166 to 178, beginning at nucleotide No. 6 and ending at nucleotide No. 26 of at least one of sequences SEQ ID NO 107 to 120, beginning at nucleotide No. 1 and ending at nucleotide No. 18 of at least one of sequences SEQ ID NO 121 to 136, beginning at nucleotide No. 39 and ending at nucleotide No. 55 of at least one of sequences SEQ ID NO 121 to 136, beginning at nucleotide No. 11 and ending at nucleotide No. 26 of at least one of sequences SEQ ID NO 139 to 144, SEQ ID NO 146, SEQ ID NO 147 and SEQ ID NO 149 to 152, beginning at nucleotide No. 5 and ending at nucleotide No. 22 of at least one of sequences SEQ ID NO 153 to 165, their corresponding DNA sequences, and sequences fully complementary to said RNA and DNA sequences, wherein said probe selectively hybridizes to RNA or DNA of only one or two species of the genus Mycobacterium.

8. The probe as claimed in claim 7, for the identification of M. xenopi, which comprises a RNA sequence beginning at nucleotide No. 59 and ending at nucleotide No. 76 of the sequence SEQ ID NO 173, a corresponding DNA sequence, or a sequence fully complementary to said RNA and DNA sequences.

9. The probe as claimed in claim 7, for the identification of M. fortuitum, which comprises a RNA sequence beginning at nucleotide No. 6 and ending at nucleotide No. 22 of the sequence SEQ ID NO 117, a corresponding DNA sequence, or a sequence fully complementary to said RNA and DNA sequences.

10. The probe as claimed in claim 7, for the identification of M. tuberculosis, which comprises a RNA sequence beginning at nucleotide No. 1 and ending at nucleotide No. 21 of the sequence SEQ ID NO 94, a corresponding DNA sequence, or a sequence fully complementary to said RNA and DNA sequences.

11. A probe comprising, as its sole nucleotide sequence, a probe sequence of no more than one hundred modified or unmodified nucleotides, said probe sequence comprising a nucleotide sequence selected from the group consisting of the following sequences of a 23S RNA of a species of the genus Mycobacterium:

beginning at nucleotide No. 137 and ending at nucleotide No. 179, beginning at nucleotide No. 206 and ending at nucleotide No. 248, beginning at nucleotide No. 269 and ending at nucleotide No. 289, beginning at nucleotide No. 289 and ending at nucleotide No. 290, beginning at nucleotide No. 341 and ending at nucleotide No. 372, beginning at nucleotide No. 645 and ending at nucleotide No. 661, beginning at nucleotide No. 1201 and ending at nucleotide No. 1242, beginning at nucleotide No. 1409 and ending at nucleotide No. 1420, beginning at nucleotide No. 1493 and ending at nucleotide No. 1515, beginning at nucleotide No. 1703 and ending at nucleotide No. 1761, beginning at nucleotide No. 1854 and ending at nucleotide No. 1876, beginning at nucleotide No. 2126 and ending at nucleotide No. 2161 of species other than M. avium, their corresponding DNA sequences, and sequences fully complementary to said RNA and DNA sequences, the numbers of the nucleotides corresponding to their position relative to the nucleotide sequence of Escherichia coli 23S ribosomal RNA, wherein said probe selective hybridizes to RNA or DNA of only one or two species of the genus Mycobacterium.

12. A primer for the specific reverse transcription of a variable region of a 23S ribosomal RNA sequence of mycobacteria into a complementary DNA sequence, said primer consisting of a sequence of no more than one hundred modified or unmodified nucleotides, said sequence comprising a nucleotide sequence of at least eight contiguous nucleotides of at least one of the following nucleotide sequences of a 23S RNA of a species of the genus Mycobacterium:

beginning at nucleotide No. 137 and ending at nucleotide No. 179, beginning at nucleotide No. 206 and ending at nucleotide No. 248, beginning at nucleotide No. 269 and ending at nucleotide No. 289, beginning at nucleotide No. 289 and ending at nucleotide No. 290, beginning at nucleotide No. 341 and ending at nucleotide No. 372, beginning at nucleotide No. 645 and ending at nucleotide No. 661, beginning at nucleotide No. 1201 and ending at nucleotide No 1242, beginning at nucleotide No. 1409 and ending at nucleotide No 1420, beginning at nucleotide No. 1493 and ending at nucleotide No 1515, beginning at nucleotide No. 1703 and ending at nucleotide No 1761, beginning at nucleotide No. 1854 and ending at nucleotide No 1876, beginning at nucleotide No. 2126 and ending at nucleotide No 2161 of species other than M. avium, their corresponding DNA sequences, and sequences fully complementary to said RNA and DNA sequences, the numbers of the nucleotides corresponding to their position relative to the nucleotide sequence of Escherichia coli 23S ribosomal RNA, wherein said primer selectively hybridizes to RNA or DNA of only one or two species of the genus Mycobacterium.

13. A primer for specific enzymatic amplification of the DNA sequence as claimed in claim 3, said primer consisting of a sequence of no more than one hundred modified or unmodified nucleotides, said sequence comprising a nucleotide sequence of at least eight contiguous modified or unmodified nucleotides of at least one of the following nucleotide sequences of a 23S RNA of a species of the genus Mycobacterium:

beginning at nucleotide No. 137 and ending at nucleotide No. 179, beginning at nucleotide No. 206 and ending at nucleotide No. 248, beginning at nucleotide No. 269 and ending at nucleotide No. 289, beginning at nucleotide No. 289 and ending at nucleotide No. 290, beginning at nucleotide No. 341 and ending at nucleotide No. 372, beginning at nucleotide No. 645 and ending at nucleotide No. 661, beginning at nucleotide No. 1201 and ending at nucleotide No. 1242, beginning at nucleotide No. 1409 and ending at nucleotide No. 1420, beginning at nucleotide No. 1493 and ending at nucleotide No. 1515, beginning at nucleotide No. 1703 and ending at nucleotide No. 1761, beginning at nucleotide No. 1854 and ending at nucleotide No. 1876, beginning at nucleotide No. 2126 and ending at nucleotide No. 2161 of species other than *M. avium*, their corresponding DNA sequences, and sequences fully complementary to said RNA and DNA sequences, the numbers of the nucleotides corresponding to their position relative to the nucleotide sequence of *Escherichia coli* 23S ribosomal RNA, wherein said primer selectively hybridizes to RNA or DNA of only one or two species of the genus Mycobacterium.

14. A reagent for detecting, identifying or detecting and identifying at least one species of mycobacteria in a biological sample, which comprises a first probe according to claim 5 that is a capture probe and a second probe according to claim 5 that is a detection probe, wherein said capture probe and said detection probe have different nucleotide sequences.

15. The reagent as claimed in claim 14, wherein the capture probe is bound directly or indirectly to a solid support.

16. The reagent as claimed in claim 14, wherein the detection probe is labeled by means of a label selected from the group consisting of: radioactive isotopes, enzymes, chromophoric chemical compounds, chromogenic compounds, fluorogenic compounds, luminescent compounds, nucleotide base analogs and biotin.

17. A reagent for detecting or identifying at least two different species of mycobacteria in a biological sample, which comprises a mixture of probes as claimed in claim 5.

18. A method of selective detection, identification or detection and identification of a species of mycobacteria in a biological sample, comprising exposing 23S ribosomal RNA extracted from bacteria contained in said sample to at least one probe as claimed in claim 7, and detecting hybridization of said probe.

19. The method as claimed in claim 18, wherein the probe is selected from the group consisting of:

a probe for identification of *M. xenopi* comprising a RNA sequence beginning at nucleotide No. 59 and ending at nucleotide No. 76 of the sequence SEQ ID NO 173, a corresponding DNA sequence, or a sequence fully complementary to said RNA and DNA sequences;

a probe for identification of *M. fortuitum* comprising a RNA sequence beginning at nucleotide No. 6 and ending at nucleotide No. 22 of the sequence SEQ ID NO 117, a corresponding DNA sequence, or a sequence fully complementary to said RNA and DNA sequences; and a probe for identification of *M. tuberculosis* comprising a RNA sequence beginning at nucleotide No. 1 and ending at nucleotide No. 21 of the sequence SEQ ID NO 94, a corresponding DNA sequence, or a sequence fully complementary to said RNA and DNA sequences.

20. A method of selective detection, identification or detection and identification of a species of mycobacteria in a biological sample, comprising denaturing genomic DNA or RNA extracted from bacteria contained in said sample, exposing said denatured DNA or RNA to at least one probe as claimed in claim 7, and detecting hybridization of said probe.

21. The method as claimed in claim 20, wherein the probe is selected from the group consisting of:

a probe for identification of *M. xenopi* comprising a RNA sequence beginning at nucleotide No. 59 and ending at nucleotide No. 76 of the sequence SEQ ID NO 173, a corresponding DNA sequences, or a sequence fully complementary to said RNA and DNA sequence;

a probe for identification of *M. fortuitum* comprising a RNA sequence beginning at nucleotide No. 6 and ending at nucleotide No. 22 of the sequence SEQ ID NO 117, a corresponding DNA sequence, or a sequence fully complementary to said RNA and DNA sequences; and a probe for identification of *M. tuberculosis* comprising a RNA sequence beginning at nucleotide No. 1 and ending at nucleotide No. 21 of the sequence SEQ ID NO 94, a corresponding DNA sequence, or a sequence fully complementary to said RNA and DNA sequences.

22. A method of selective detection, identification or detection and identification of a species of mycobacteria in a biological sample, comprising exposing DNA obtained by reverse transcription of 23S ribosomal RNA of bacteria contained in said sample to at least one probe as claimed in claim 7, and detecting hybridization of said probe.

23. The method as claimed in claim 22, wherein the probe is selected from the group consisting of:

a probe for identification of *M. xenopi* comprising a RNA sequence beginning at nucleotide No. 59 and ending at nucleotide No. 76 of the sequence SEQ ID NO 173, a corresponding DNA sequence, or a sequence fully complementary to said RNA and DNA sequences;

a probe for identification of *M. fortuitum* comprising a RNA sequence beginning at nucleotide No. 6 and ending at nucleotide No. 22 of the sequence SEQ ID NO 117, a corresponding DNA sequence, or a sequence fully complementary to said RNA and DNA sequences; and a probe for identification of *M. tuberculosis* comprising a RNA sequence beginning at nucleotide No. 1 and ending at nucleotide No. 21 of the sequence SEQ ID NO 94, a corresponding DNA sequence, or a sequence fully complementary to said RNA and DNA sequences.

24. The fragment as claimed in claim 1, wherein said nucleotide sequence is selected from the group consisting of the following nucleotide sequences of the 23S RNA:

beginning at nucleotide No. 137 and ending at nucleotide No. 179, beginning at nucleotide No. 206 and ending at nucleotide No. 248, beginning at nucleotide No. 289 and ending at nucleotide No. 290 of a 23S ribosomal RNA of species other than *M. tuberculosis* and *M. fortuitum*, beginning at nucleotide No. 341 and ending at nucleotide No. 372, beginning at nucleotide No. 1201 and ending at nucleotide No. 1242, beginning at nucleotide No. 1409 and ending at nucleotide No. 1420 of a 23S ribosomal RNA of species other than *M. tuberculosis*, *M. marinum*, *M. scrofulaceum*, *M. avium* TMC 724, *M. leprae*, *M. kansasii*, *M. asiaticum*, *M. ulcerans* ATCC 19423, *M. malmoense* ATCC 29571, *M. gordonae*, *M. lactae*

ATCC 25854, *M. aurum* ATCC 23366, *M. vaccae* ATCC 15483 and *M. neoaurum* ATCC 25795, beginning at nucleotide No. 1493 and ending at nucleotide No. 1515, beginning at nucleotide No. 1703 and ending at nucleotide No. 1761, their corresponding DNA sequences, and sequences fully complementary to said RNA and DNA sequences.

25. The fragment as claimed in claim 1, wherein said nucleotide sequence is selected from the group consisting of the following nucleotide sequences of the 23S RNA:

beginning at nucleotide No. 137 and ending at nucleotide No. 179, beginning at nucleotide No. 206 and ending at nucleotide No. 248, beginning at nucleotide No. 269 and ending at nucleotide No. 289 of a 23S ribosomal RNA of species other than *M. tuberculosis* and *M. fortuitum*, beginning at nucleotide No. 289 and ending at nucleotide No. 290 of a 23S ribosomal RNA of species other than *M. tuberculosis* and *M. fortuitum*, beginning at nucleotide No. 341 and ending at nucleotide No. 372, beginning at nucleotide No. 645 and ending at nucleotide No. 661 of a 23S ribosomal RNA of species other than *M. tuberculosis* and *M. fortuitum*, beginning at nucleotide No. 1201 and ending at nucleotide No. 1242, beginning at nucleotide No. 1493 and ending at nucleotide No. 1515, beginning at nucleotide No. 1703 and ending at nucleotide No. 1761, beginning at nucleotide No. 1854 and ending at nucleotide No. 1876 of a 23S ribosomal RNA of species other than *M. tuberculosis*, *M. kansasii* and *M. fortuitum*, their corresponding DNA sequences, and sequences fully complementary to said RNA and DNA sequences.

26. A method of selective detection, identification or detection and identification of a species of mycobacteria in a biological sample, comprising exposing 23S ribosomal RNA extracted from bacteria contained in said sample to at least one probe as claimed in claim 5, and detecting hybridization of said probe.

27. A method of selective detection, identification or detection and identification of a species of mycobacteria in a biological sample, comprising denaturing genomic DNA or RNA extracted from bacteria contained in said sample, exposing said denatured DNA or RNA to at least one probe as claimed in claim 5, and detecting hybridization of said probe.

28. A method of selective detection, identification or detection and identification of a species of mycobacteria in a biological sample, comprising exposing DNA obtained by reverse transcription of 23S ribosomal RNA of bacteria contained in said sample to at least one probe as claimed in claim 5, and detecting hybridization of said probe.

* * * * *

UNITED STATES PATENT AND TRADEMARK OFFICE
CERTIFICATE OF CORRECTION

PATENT NO. : 5,703,217
DATED : December 30, 1997
INVENTOR(S) : Claude MABILAT and Richard CHRISTEN It is certified that error appears in the above-identified patent and that said Letters Patent is hereby corrected as shown below:

On the title page, in item [56], please add the following:

FOREIGN PATENT DOCUMENTS

--91/09057        01/1993        France--
--90/07249        12/1991        France--
--WO-88/03957     06/1988        WIPO--

OTHER PUBLICATIONS

--W. LIESACK et al., "Complete Nucleotide Sequence of the Mycobacterium leprae 23 S and 5 S rRNA Genes Plus Flanking Regions and their Potential in designing diagnostic oligonucleotide probes," Vol. 281, No. 1,2, April 1991.--

--W. LIESACK et al., "Development of a Highly Specific Diagnostic 23S rDNA Oligonucleotide Probe for Mycobacterium leprae," Letters In Applied Microbiology, Vol. 11, No. 2, April 27, 1990.--

UNITED STATES PATENT AND TRADEMARK OFFICE
CERTIFICATE OF CORRECTION

PATENT NO. : 5,703,217
DATED : December 30, 1997
INVENTOR(S) : Claude MABILAT and Richard CHRISTEN It is certified that error appears in the above-identified patent and that said Letters Patent is hereby corrected as shown below:

On the title page, in Attorney, Agent, or Firm, change "Oliffe" to --Oliff--.

Signed and Sealed this

Thirty-first Day of March, 1998

Attest:

BRUCE LEHMAN

Attesting Officer

Commissioner of Patents and Trademarks